(12) United States Patent
Niehaus et al.

(10) Patent No.: US 8,623,810 B2
(45) Date of Patent: Jan. 7, 2014

(54) PROTEASE FOR WOUND CONDITIONING AND SKIN CARE

(75) Inventors: Frank Niehaus, Heppenheim (DE); Jürgen Eck, Bensheim (DE); Renate Schulze, Bensheim (DE); Michael Krohn, Lorsch (DE)

(73) Assignee: B.R.A.I.N. Biotechnology Research and Information Network AG, Zwingenberg (DE)

( * ) Notice: Subject to any disclaimer, the term of this patent is extended or adjusted under 35 U.S.C. 154(b) by 0 days.

(21) Appl. No.: 13/254,157

(22) PCT Filed: Mar. 3, 2010

(86) PCT No.: PCT/EP2010/001328
§ 371 (c)(1),
(2), (4) Date: Nov. 17, 2011

(87) PCT Pub. No.: WO2010/099955
PCT Pub. Date: Sep. 10, 2010

(65) Prior Publication Data
US 2012/0093788 A1    Apr. 19, 2012

(30) Foreign Application Priority Data

Mar. 3, 2009 (EP) ...................................... 09003063

(51) Int. Cl.
| | |
|---|---|
| *C12N 9/48* | (2006.01) |
| *C12N 9/50* | (2006.01) |
| *C12N 15/52* | (2006.01) |
| *C12N 15/57* | (2006.01) |
| *C12P 21/00* | (2006.01) |
| *A61K 38/43* | (2006.01) |
| *A61K 38/48* | (2006.01) |
| *A61K 48/00* | (2006.01) |
| *A61P 17/02* | (2006.01) |

(52) U.S. Cl.
USPC .................. 514/1; 514/12; 514/44; 424/93.2; 424/94.1; 424/94.64; 435/69.1; 435/212; 435/219; 530/350; 536/23.5

(58) Field of Classification Search
USPC ............ 424/93.2, 94.1, 94.64; 435/69.1, 212, 435/219; 514/1, 12, 44; 530/350; 536/23.5
See application file for complete search history.

(56) References Cited

U.S. PATENT DOCUMENTS 6,458,564 B1 * 10/2002 Darrow et al. ............... 435/69.7
7,144,721 B1    12/2006 Pritchard

FOREIGN PATENT DOCUMENTS

| WO | WO 2007/138361 | * 12/2007 |
|---|---|---|
| WO | WO 2007/138361 A | 12/2007 |

OTHER PUBLICATIONS

Borovsky et al, Eur. J. Biochem. 237:279-287, 1996.*
Borovsky, D., et al., Molecular Sequencing and Modeling of *Neobellieria bullata* Trypsin. Evidence for Translational Control by *Neobellieria* Trypsin-Modulating Oostatic Factor, European J. of Biochem., 1996, 237:279-287.
Casu, R.E., et al., Isolation of a Trypsin-Like Serine Protease Gene Family from the Sheep Blowfly *Lucilia cuprina*, Insect Molecular Biology, 1994, 3:159-170.
Chambers, L., et al., Degradation of Extracellular Matrix Components by Defined Proteinases from the Greenbottle Larva *Lucilia sericata* Used for the Clinical Debridement of Non-Healing Wounds, British J. of Dermatology, 2003, 148:14-23.

* cited by examiner

*Primary Examiner* — Kevin Hill
(74) *Attorney, Agent, or Firm* — Pillsbury Winthrop Shaw Pittman LLP

(57) ABSTRACT

We have identified by molecular cloning a protease which originates from the larvae of *Lucilia sericata* and which was termed debrilase due to its activities useful for debridement of wounds. Described is a nucleic acid molecule encoding a serine protease having the ability to cleave fibrin and casein which is (a) a nucleic acid molecule encoding the serine protease comprising or consisting of the amino acid sequence of SEQ ID NO: 4 as well as to nucleic acid molecules encoding precursors or fragments of said serine protease; (b) a nucleic acid molecule comprising or consisting of the nucleotide sequence of SEQ ID NO: 3; (c) a nucleic acid molecule encoding a serine protease the amino acid sequence of which is at least 80% identical to the amino acid sequence of (a), preferably at least 85% identical, more preferably at least 90% identical, and most preferred 95% identical; (d) a nucleic acid molecule comprising or consisting of a nucleotide sequence which is at least 80% identical to the nucleotide sequence of (b), preferably at least 85% identical, more preferably at least 90% identical, and most preferred 95% identical; (e) a nucleic acid molecule which is degenerate with respect to the nucleic acid molecule of (b) or (d); or (f) a nucleic acid molecule corresponding to the nucleic acid molecule of any one of (a) to (d) wherein T is replaced by U.

18 Claims, 7 Drawing Sheets

Figure 1:
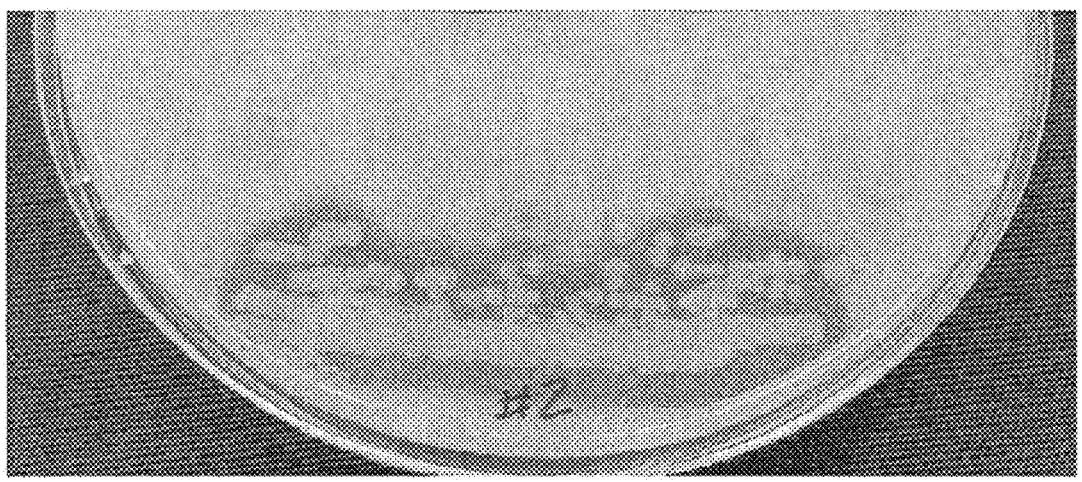

Figure 2
A
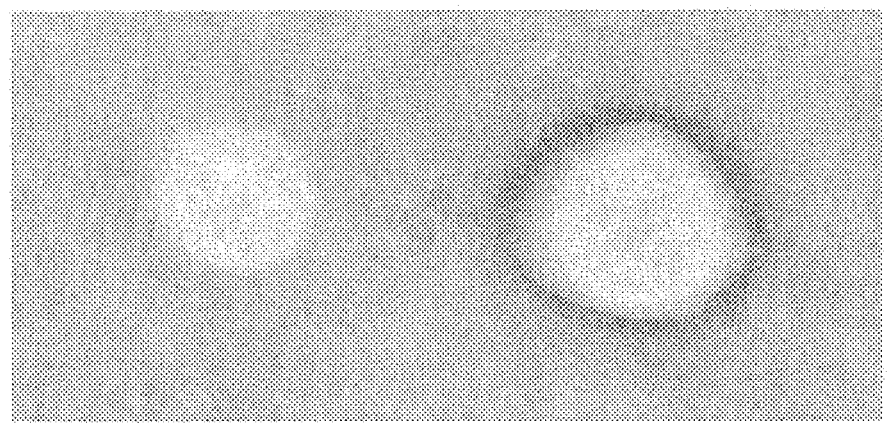
E. coli control clone      E. coli clone comprising debrilase gene
B
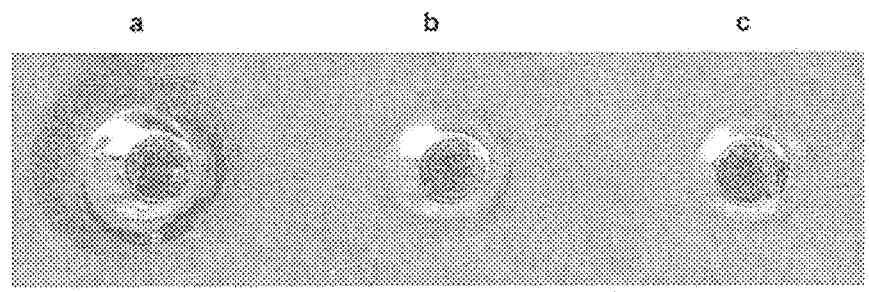

Figure 3
A)
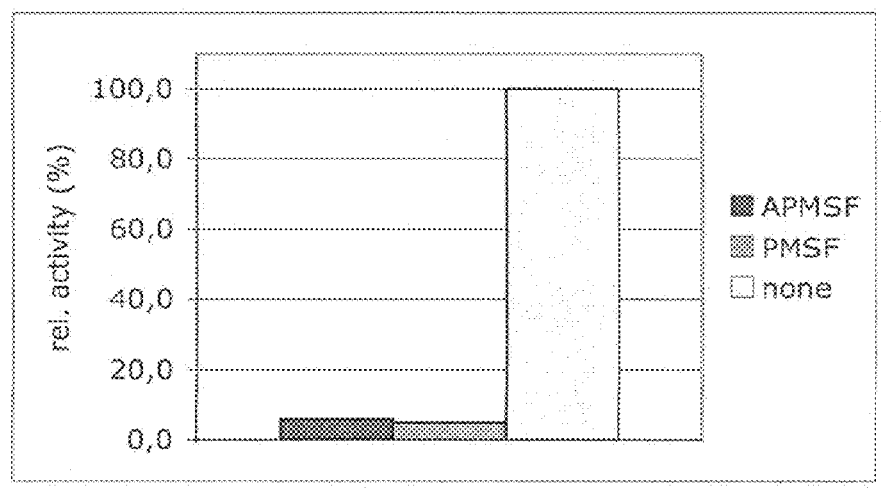
B)
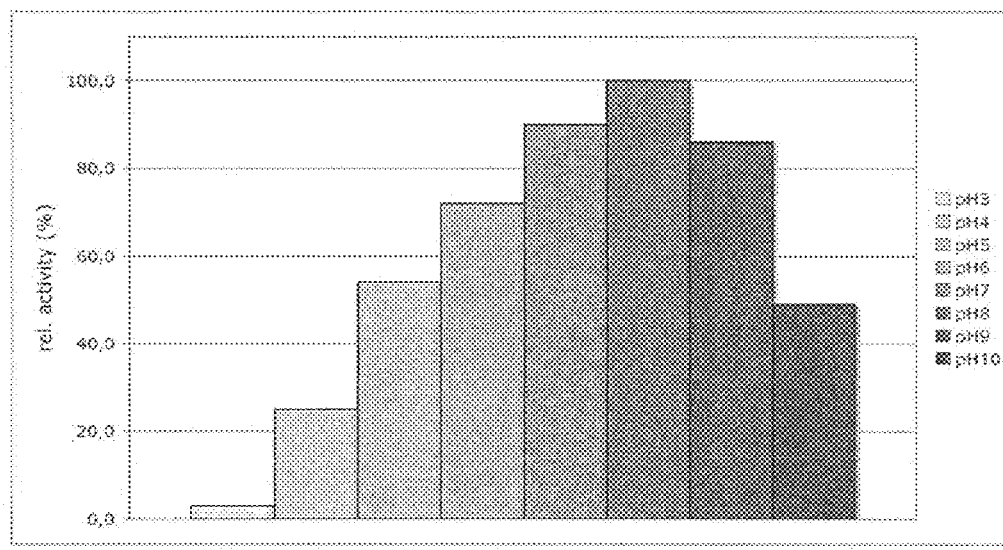

PAR 2-activation

Figure 5A

Protein Sequence Alignment

```
>gi|1717788|sp|P51588.1|TRYP_SARBU  RecName: Full=Trypsin; Flags: Precursor
 gi|1177316|emb|CAA64354.1|  trypsin-like enzyme [Sarcophaga bullata]
Length=254

Score =  427 bits (1099),  Expect = 3e-118, Method: Compositional matrix
adjust.
 Identities = 195/254 (76%), Positives = 227/254 (89%), Gaps = 0/254 (0%)

Query  1    MFRFVALFAFVSCALAGAIPNHLDSRIVGGVDTTIQAHPYQVSLQTNPGFRPCGGSIISS   60
            M RF+A+FA V+CALAG +P+HLD+RIVGGVDTTI+AHP+QV LQ       RPCGGSIIS+
Sbjct  1    MLRPIAVFALVTCALASTLPSHLDSRIVGGVDTTIKAHPYQVPLQRAALSHPCGGSIISS   60

Query  61   DIIVTAAHCNQSYKAYQPKVRLGSTEYDNGGELVAVKSFKYHEGYNPETMVNDVAVIKIA  120
            D++VTAAHCNQSY A Q KVRLGST Y+ GGELV+VK+FK+HEGYNP+T+VNDVA+IKIA
Sbjct  61   DLVVTAAHCNQSYTASQIKVRLGSTIYNEGGELVSVKAFKFHEGYNPKTVVNDVALIKIA  120

Query  121  TPVRESSKVRYVKLAEKTPATSTPAVVTCKGSKCFLPCQTAPKVLQEVEVDIVEEKTCAS  180
            TPVRESSK+RY++LA++TP TSTPAVVT+KG+KCFL C + PK LQ+VEVDIV++K CAS
Sbjct  121  TPVRESSKIRYTPLADRTPPTSTPAVVTSKGTKCFLTCVSLPKTLQSVEVDIVDQKACAS  180

Query  181  SEKKYGDDINSTNLCAYAVKKDACQSDSKSPLVANNKLVGVVSWGKGCALAGYPGVYCDV  240
            +E+KYG   I+++N+C+YA+KKDACQ+DS+SPLVAN +LV +VS+G GCA    GYPGV+CDV
Sbjct  181  NEFKYGSQIQDTNVCAYALKKDACQSDSGSPLVANNQLVSIVSWGSGCARVGYPGVFCDV  240

Query  241  ATVPSWIEKTAKSL    254
            +VPSWIEKTAK L
Sbjct  241  DSVPSWIEKTAKEL    254
```

Figure 5B cDNA Sequence Alignment

```
>gi|1177319|emb|X94891.1|NBTRYPSIN  N.bullata mRNA for trypsin-like protein
Length=836

Score =  571 bits (632),  Expect = 2e-159
 Identities = 588/768 (76%), Gaps = 6/768 (0%)
 Strand=Plus/Plus Query  1    ATGTTCCGCTTTGTAGCTCTATTCGCTTTCGTTAGCTGTGCCTTGGCCGGCGCTATTCCC  60
            ||  |  | ||| || |  ||  |   |||||  |  | |  |  |  |||||| |
Sbjct  1    ATGTACCTTTCATATGTATTCTCTTTAGTTAACTGTGCTTGGCCAGCACTCTGCCC      60

Query  61   AATGATTTGGATGGCCGCATTGTCAATGGTGTGGATACCACCATTCAGGCCCATCCCTAT  120
            |  |||||| ||||  | ||| | ||| | | ||||| || |||||  ||| ||| |||
Sbjct  61   AACGATTTGGATGGTCTATTGTTAACGGTGTTGATACTACAATTCAGGCCCATCCTTAT     120

Query  121  CAGGTTTCTTTGCAAACGAACAATGTTTC---CATTTCTGCGGTGCTTCCATCGTCAGC  177
            ||  |  |  || ||||      | ||      || || | ||| |||||| |
Sbjct  121  CAGGTTCCATTGCAAA----ATGCTGCTCTCAGTCATTTCTGTGGGATCCATTATCAGT    177

Query  178  GAAGACATTATTGTAACTGCTGCTCATTGCATGCAAATCCTACAAGGCCTACCAATTCAA  237
            |||| | | |||| ||||||  |||| |   ||| | | |    |  ||| ||||| ||
Sbjct  178  GAAGATCTAGTTGTTACTGCTGCTCATTGTATGCAATCCTATACGGCTTCTAAATTAA     237

Query  238  GTGCGTTTGGGTTCCACTGAATACGATAATGGTGGTGAATTGTTGCCGTCAAGTCTTTC  297
            || | |||| | |||||| ||||  ||| ||||| |||||||| | |   |||  |||
Sbjct  238  GTGCGTTTGGCTCTACTATATACAATGAAGGAGGTAAATTGGTATCAGTAAAGCTTTT     297

Query  298  AAATACCACGAAGGTTACAATCTCGAAACCATGGTTAATGATGTTGCCGTTATCAAATTA  357
            ||| |||| ||||| |||| | || |  | | |||||  ||| |||||| ||| |||
Sbjct  298  AAATTCCACGAAGGTTACAATTCTAGCACAACGTGAATGACTGGCTCTATTAAATTG     357

Query  358  GCCACTCCAGTGCGTGAATCTTCGAAGTACGTTATGTTAAATGGCTGAGAAGACACCT  417
            ||||||||| |  | |||  | |||| | || |||  ||   || | |||| |||||
Sbjct  358  CCAACTCCACTATGTGAATCCTCAAAATCCTTACATTCGTTGCTGATGTACTCCA       417

Query  418  GCTATTGCGCGCCAAGTGTCGTTACTGGTTGGGTTCTAAGTGCTTCTTGTTCTGCCAA  477
            |||| | | || ||| | |  ||||  ||| ||||||||  | |||||||  |||  |
Sbjct  418  CCTACTGTACGCCGGCTGTCGTTACTGGCTGGGTACCAAGTGTTTCTTAACCTCTGTT     477

Query  478  ACTGCCCCTAAAGTTTTGGAAAAGGTTGAGGTCGATATTGTTGATGACAGACCTGCGCT  537
            |||    ||||||| |  | |||| ||  | ||| |||  |||| || |  | ||| |
Sbjct  478  AGTTTGCCAAGACTTTGCAAGAAGGTTGAAGTTTATATTGTTGATCAGAAAGCCTGCGCT   537

Query  538  TCCAGCGAATACAAATATGCTGATGACATCAAGGAAACTATGTTGTGTCTTATCGTGTT  597
            |||  |  ||||||  ||||||   |   || || || ||  ||| |||  ||   ||
Sbjct  538  TCCAATGAATTTAAATATGCAGCCAAATACAAAACTATGTATGTCTTACGCTTA      597

Query  598  AAGAAGGATGCTTGGCCAAGGTGATTCTGCTGGTCTTTGGTTGCAACAACAAATTGGTC  657
            |||| ||||||| | ||||| ||||| | ||| ||    | |    || | | |||  |
Sbjct  598  AAAAAGGATGCTTGCTCAAGCGACTCTGCTGGCCATTAGTGCTAATCAATTGCTC       657

Query  658  GGTGTTGTTCCTCCGGGTAAAGGTTGTGCCCTTGCTGCTATCCCGGTGTATACTGCGAT  717
            |  | | | |||| | || | ||  |||| ||||| ||  || | ||| ||| | |||
Sbjct  658  GCTATTGTTCTTGCCGTAGTGGTTGCCGTGCGTCGCTATCCTGTTATTCTCTGAT     717

Query  718  GTTGCTACTGTCGGCAGCTGGATTGAAAGACTGCCAAGAGTTTGTAA  765
            |||  ||| || ||  | |||  |||||| |||||| ||| | ||||
Sbjct  718  GTGCCTACTGTACGCTCATGCAATGAAAAGACTGCAAGGAATTCTAA     765
```

PROTEASE FOR WOUND CONDITIONING AND SKIN CARE

RELATED APPLICATIONS

This application is the National Phase of international Application No. PCT/EP2010/001328, filed Mar. 3, 2010, which designated the U.S. and that International Application was published under PCT Article 21(2) in English, and claims priority to European Application No. 09003063.6, filed Mar. 3, 2009, all of which applications are incorporated herein by reference in their entirety.

The invention relates to pharmaceutical and cosmetical compositions as well as medical articles comprising a protease, termed debrilase, from *Lucilia sericata* for use in wound conditioning and skin care. Debrilase was identified using the larval transcriptome, i.e. mRNA preparations and conversion into cDNA, and prepared using recombinant techniques and subsequent expression in suitable host cells. The protease of the invention has fibrinolytic, ca seinolytic and PAR-2 (protease-activated receptor 2) activating activity. In one embodiment, compositions comprising debrilase are provided for the cleaning of slow or non-healing wounds from necrotic cells, tissue and fibrin cuffs, known as debridement. In another embodiment cosmetic uses of debrilase in the field of skin care and smoothening are proposed.

The invention further relates to a nucleic acid molecule encoding a serine protease having the ability to cleave fibrin and casein, which is a nucleic acid molecule encoding the serine protease comprising or consisting of the amino acid sequence of SEQ ID NO: 4 as well as to nucleic acid molecules encoding precursors or fragments of said serine protease. Furthermore, it relates to a nucleic acid molecule comprising or consisting of the nucleotide sequence of SEQ ID NO: 3 and a nucleic acid molecule encoding a serine protease the amino acid sequence of which is at least 77%, more preferred at least 80%, even more preferred at least 85% and most preferred at least 90% identical to the nucleotide sequence of SEQ ID NO: 3. Any of the above nucleic acids, wherein T is replaced by U are also within the scope of the invention.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Wound healing has three distinct phases: (1) inflammation; (2) cell migration and proliferation; and (3) remodelling. In the inflammatory phase proteases are released by cells of the immune system. Various lymphokines are secreted from neutrophils and macrophages that modulate the next phase of the wound healing. The second phase is designated proliferation phase and includes fibroblast migration, proliferation and the synthesis of new extracellular matrix molecules. These events appear to occur in a definite order where extracellular matrix molecules including fibronectin, collagen and proteoglycans are secreted into the granulation bed. The inflammatory phase peaks at 3 days. The second phase of wound healing normally peaks at approximately one to two weeks after injury and is followed by a much longer third phase of tissue remodelling that begins within weeks and may last several months. During the remodelling phase, the connective tissue matrix matures as the disorganized collagen fibers are replaced by thicker, more aligned collagen molecules. This tissue remodelling eventually contributes to the tensile strength of the wound and is sometimes accompanied by scar formation.

A skin lesion virtually always involves an injury of the blood vessels. Wound healing therefore also comprises the process of coagulation, being a complex process by which blood forms clots. It is an important part of hemostasis whereby a damaged blood vessel wall is covered by a platelet and fibrin containing clot to stop bleeding and begin repair of the damaged vessel. Disorders of coagulation can lead to an increased risk of hemorrhage and/or thrombosis. Coagulation is initiated almost instantly after an injury to the blood vessel has damaged the endothelium. Platelets immediately form a hemostatic plug at the site of injury (primary hemostasis). Secondary hemostasis occurs simultaneously where coagulation factors in the blood plasma respond in a complex cascade to form fibrin strands which strengthen the platelet plug. The coagulation cascade of secondary hemostasis has two pathways, the contact activation pathway (formerly known as the intrinsic pathway) and the tissue factor pathway (formerly known as the extrinsic pathway) both leading to fibrin formation. It is now known that the primary pathway for the initiation of blood coagulation is the tissue factor pathway. The pathways are a series of reactions, in which a zymogen (inactive enzyme precursor) of a serine protease and its glycoprotein co-factor are activated to become active components that then catalyze the next reaction in the cascade, ultimately resulting in cross-linked fibrin. The coagulation factors are generally serine proteases, except for FVIII and FV which are glycoproteins and Factor XIII which is a transglutaminase. The coagulation cascade is classically divided into three pathways. The tissue factor and the contact activation pathway both activate the "final common pathway" of factor X, thrombin and fibrin.

Fibrin is a protein involved in the clotting of blood. It is a fibrillar protein that is polymerised to form a hemostatic plug or clot—in conjunction with platelets—over a wound site. Fibrin is made from its zymogen fibrinogen, a soluble plasma glycoprotein that is synthesised by the liver. In the coagulation cascade the zymogen prothrombin is activated to the serine protease thrombin, which is responsible for converting fibrinogen into fibrin. Fibrin is then cross linked by factor XIII to form a clot.

Plasmin proteolytically cleaves fibrin into fibrin degradation products which inhibits excessive fibrin formation. Plasmin is generated by proteolytic cleavage of plasminogen, a plasma protein synthesized in the liver. This cleavage is catalyzed by tissue plasminogen activator (t-PA) which is synthesized and secreted by the endothelium. Plasminogen is entrapped during clot formation and is slowly activated when the wound has stopped bleeding and the clot is broken down.

The disintegration of the clot during wound healing is an important step to allow for matrix formation and remodelling as described above. It is thought that one potential cause for slow healing or chronic wounds is a lack of fibrinolysis. So called "fibrin cuffs", consisting of fibrin, laminin, fibronectin, tenascin, collagen and leucocytes hamper the exchange of nutrients, growth factors and gas, leading to anoxia, ulcus formation and preventing angiogenesis. The proteolytic dissolution of these "fibrin cuffs" supports neovascularisation, invasion of leucocytes, migration of fibroblasts, formation of a new epithelium and induces cell proliferation and migration. Furthermore, the healing of wounds is delayed by the presence of pus, tissue debris, bacteria, and exudates which can be removed by debridement agents.

Debridement is defined as the removal of non-vital tissue from wounds. In chronic wounds, debridement means the elimination of necrosis as well as the clearing away of wound dressings, foreign bodies, and other non-vital substances. Sufficient debridement represents one basic prerequisite for a non-delayed wound-healing process. In addition to treating the causal factors for delayed wound healing, debridement should be the first step in an adequate phase-adapted wound-bed preparation for chronic wounds. Different methods for debridement in chronic wounds have been described such as surgery, maggot therapy, laser, ultrasound, hydrotherapy, wet-to-dry method, autolysis, proteolytic enzymes, osmotic or chemical debridement.

Debridement agents rapidly digest necrotic tissue without injury to living cells, thereby speeding up the healing processes. The search for such debridement agents has included the employment of a wide variety of plant and animal materials, such as maggots or blowfly larvae, but also of enzymes like papain, bromelain and ananain from plant origin (e.g. U.S. Pat. No. 6,548,556, EP 0194647 B1, U.S. Pat. No. 5,106, 621), proteases from microbial origin (e.g. protease from *Vibrio* spec., U.S. Pat. No. 5,145,881; thermolysin from *Bacillus* spec., WO 03/088993 A1, US 2003/0198632 A1) and from animals (e.g. trypsin and chymotrypsin from fish, U.S. Pat. No. 6,846,485). Some debriding enzymes function as protease-inhibitors either within the coagulation cascade (thrombin inhibitory nexin-1 (PN-1), U.S. Pat. No. 5,112, 608) or in the acute-phase-reaction (alpha1-antitrypsin. U.S. Pat. No. 6,262,020). The primary purpose of debriding enzymes is to clean a wound of all of the various necrotic tissue elements and to thin out tenacious exudative secretions. Appropriately applied proteolytic enzymes cleanse infected surfaces of their inflammatory exudate without harming the living tissues. They facilitate the drainage of areas of located purvulent, sanguineous and fibrinous accumulations, promote the liberation of hidden bacteria rendering them accessible to the immune defence system.

The enzymatic action of debriding enzymes can be utilised for non-healing wounds (e.g. Lobmann et al., Proteases and the diabetic foot syndrome: Mechanisms and therapeutic Implications. Diabetes Care 28 (2005), 461-471), but they can also be of benefit for the treatment of inflammatory skin diseases such as psoriasis and eczema and the like, and less severe skin conditions, such as wrinkles, acne and dry skin, as disclosed for example in U.S. Pat. Nos. 4,524,136; 5,439,935; 5,441,740; 5,554,366; 5,853,705 and 6,780,444. Commercial products comprising such enzymes are also available, e.g. Accuzyme® (papain) and Granulex® (trypsin), the application of which is limited for debridement of wounds.

There has been a continuing effort to find better wound debridement enzymes. Some of the criteria for a highly preferred wound debridement enzyme are at least one and preferably more such as all of the following: it should be capable of rapid digestion of fibrin, denatured collagen, elastin and exudate; it should spare normal appearing human skin tissues; it should be non-toxic and non-irritating to wounds; it should be easily prepared, stable and readily applicable. As an example, stable concentrated enzymatic compositions suitable for storage under ambient conditions, while maintaining enzymatic activity and kits comprising enzymatic compositions are described in WO 2007/074454 A2.

Several approaches for dealing with chronic wounds comprise the use of dressings keeping the wound moist to support the viability of cells of the immune system infiltrating the wound.

For wound management, the use of proteases, i.e. exo- and endopeptidases, as well as the use of protease inhibitors was proposed.

A silicone-based device for controlled release of enzymes for the proteolytic debridement of wounds was described by Bott et al. (A silicone-based controlled-release device for accelerated proteolytic debridement of wounds, Wound Repair Regen. (2007) 15: 227-35) using a protease of the subtilisin family. Similarly, U.S. Pat. No. 7,368,128 describes a dressing for sustained release of debriding enzymes consisting of an absorbent material layer and a degradable polymeric material.

For centuries, maggots were known to have beneficial effects on wounds. The method of Maggot Debridement Therapy (MDT) was adopted and routinely used in the United States throughout the 1930s and early 1940s, but MDT was replaced with the introduction of penicillin and modern surgical procedures (Child F S, Roberts E F. The treatment of chronic osteomyelitis with live maggots. *New York State J Med* 1931; 31: 937-43; Teich S, Myers R A M. Maggot therapy for severe skin infections. *South Med J* 1986; 79: 1153-5; Church J C T. Larvae therapy in modern wound care: A review. *Primary Intention* 1999; May: 63-8; Sherman R A, Hall M J R, Thomas S. Medicinal maggots: An ancient remedy for some contemporary afflictions. Ann Rev Entomol 45 (2000): 55-81, Courtenay, M. et al., Larva therapy in wound management, J. R. Soc. Med. 93 (2000): 72-74).

Application of maggots to a wound is frequently perceived as unpleasant and even painful by the patient. Nevertheless, the larvae of different insect species are utilised for the cleaning and healing of conventionally untreatable wounds. Maggots of certain fly species feed on necrotic tissue and through this debriding activity assist the healing of chronic soft-tissue wounds, such as pressure and venous stasis ulcers, diabetic foot infections, and postoperative wounds, which are resistant to surgical or antibiotic intervention (Sherman R A, 1998, Maggot debridement in modern medicine. Infect Med 15: 651-6, Sherman R A, Hall M J R, Thomas S., 2000, Medicinal maggots: An ancient remedy for some contemporary afflictions. Ann Rev Entomol 45: 55-81).

Medicinal maggots exert three main actions: 1) they debride (clean) wounds by dissolving the dead (necrotic), infected tissue; 2) they disinfect the wound, by killing bacteria; and 3) they stimulate wound healing.

Horobin et al. (2006) describe MDT with *Lucille sericata* larvae or green bottle fly maggots which are applied to chronic wounds to aid healing by triggering fibroblast migration and matrix remodelling (Horobin et al., Promotion of human dermal fibroblast migration, matrix remodelling and modification of fibroblast morphology within a novel 3D model by *Lucilia sericata* larval secretions, J Invest Dermatol. 126: 1410-1418). Previously, they have characterized certain enzymatic activities present within maggot excretions/secretions (ES) (Horobin et al. 2003, Maggots and wound healing: an investigation of the effects of secretions from *Lucille sericata* larvae upon interactions between human dermal fibroblasts and extracellular matrix components. Br. J. Dermatol. 148: 923-933).

The bactericidal activity of secretions from *Lucille sericata* maggots towards typical wound colonizers such as *Micrococcus luteus* and *Staphylococcus aureus* was shown using third instar larvae (Daeschlein, G. et al., 2007, In vitro antibacterial activity of *Lucilia sericata* maggot secretions, Skin Pharmacol. Physiol. 20: 112-115).

Interactions between fibroblasts and the surrounding extracellular matrix play a crucial role in tissue formation, influencing fibroblast proliferation, migration, and tissue remodelling. The postulated mechanisms by which maggots enhance tissue formation within wounds may be via the promotion of fibroblast motility, acceleration of extracellular matrix remodelling and coordination of cellular responses, providing for a wider distribution of viable fibroblasts. It was shown that *L. sericata* ES-products promoted fibroblast migration upon a fibronectin-coated surface and that this was related to the degradation of fibronectin by serine proteases within maggot excretion/secretions (Chambers et al. 2000, Degradation of extracellular matrix components by defined proteinases from the greenbottle larva *Lucilia sericata* used for the clinical debridement of non-healing wounds, Brit J Dermatol. 148: 14-23).

A large and diverse family of serine protease genes was identified in first instar larval cDNA of the sheep blowfly, *Lucilia cuprina* (Elvin et al. 1994, An estimate of the number of serine protease genes expressed in sheep blowfly larvae (*Lucille cuprina*)" Insect Molecular Biol 3: 105-115). Two chymotrypsin-like proteases were purified from the ES-products of first instar larvae of *Lucille cuprina* (Casu et al. 1994, Excretory/secretory chymotrypsin from *Lucilia cuprina*: purification, enzymatic specificity and amino acid sequence deduced from mRNA, Insect Molecular Biol 3: 201-211). Various protease inhibitors active against both trypsin- and chymotrypsin-like serine proteases were used to characterize gut proteases from *Lucilia cuprina* by in vitro feeding assays (Casu et al. 1994, Isolation of a trypsin-like serine protease gene family from the sheep blowfly *Lucille cuprina*, Insect Molecular Biol 3: 159-170). Significant larval growth retardation, was observed on feeding first instar larvae with trypsin inhibitors, particularly soybean trypsin inhibitor. Feeding of chymostatin, a specific chymotrypsin inhibitor, resulted in no significant growth retardation. This information suggests that trypsin-like serine proteases are probably the major gut digestive enzymes.

Chambers et al. (2003, Degradation of extracellular matrix components by defined proteinases from greenbottle larva *Lucilia sericata* used for the clinical debridement of non-healing wounds, British J. Dermatol 148: 14-23) describe proteases with activities against fibrin and extracellular matrix components in first to third instar larvae of the greenbottle fly *Lucille sericata*. They found the highest specific activity in excretions of the early larval stages (first and second instar). Proteases with chymotrypsin and trypsin-like activities contained in larval excretory/secretory (ES) products are thought to contribute to wound debridement by removal of necrotic tissue. Three classes of proteolytic enzyme were detected in the secretions using fluorescein isothiocyanate-labelled casein as a model substrate: serine proteinases (pH optima 8-9) of two different subclasses (trypsin-like and chymotrypsin-like), aspartyl proteinase (pH optimum 5) and a metalloproteinase (pH optimum 9) with exopeptidase characteristics. Using skin-relevant ECM components as substrates *L. sericata* ES products solubilized fibrin clots and degraded fibronectin, laminin and acid-solubilized collagen types I and III.

Despite these results, until today scientists and medical doctors seek for the active principle behind the huge amount of proteolytically active proteins in the larvae. It is known that larval secretions are capable of degrading the extracellular matrix (ECM)/wound components, fibronectin, laminin and collagens I, III, IV and V. These macromolecules are found in the slough of chronic wounds and also make up the "fibrin cuffs" that are predominant in chronic ulcers. The degradation of laminin and fibronectin by larval secretions is inhibited by PMSF, but not significantly by APMSF or by the metalloproteinase inhibitor 1,10-phenanthroline. The activity of the larval secretions exhibit a pH optimum of 8.0-8.5 (Chambers et al. 2000, Degradation of extracellular matrix components by defined proteinases from the greenbottle larva *Lucilia sericata* used for the clinical debridement of non-healing wounds, Brit J. Dermatol. 148: 14-23), which is not consistent with the wide pH-range from acidic to basic in chronic wounds. Therefore, there is a need for debriding enzymes with activity in a much more extensive pH-range as that described for the larval secretions.

In U.S. Pat. No. 7,144,721 B1 it is speculated that the main proteolytic activity in larval secretions is a serine proteinase activity and that there are two types of serine proteinase activity present; one derived from a chymotryptic enzyme and one derived from a tryptic enzyme. US 2008/0108551 A1 provides evidence that degradation of the extracellular matrix is an important step in protease mediated wound healing by *Lucilia sericata*. In said application a serine protease and a metalloprotease isolated from *Lucilia sericata* excretory/secretory products are postulated, which degrade the extracellular matrix component fibronectin or increase cell migration, respectively. Apparently, the resulting biologically active degradation products of fibronectin promote wound healing. In WO 2007/138361 A3 a chymotrypsin from *Lucilia sericata* larvae for use in the treatment of wounds is disclosed. Further proteins which are apparently involved in wound healing like a nuclease (WO 2007/122424 A2) and a ligand for the toll-like receptor (US 2005/0053597 A1) were identified in the secretion products of larvae from *Lucilia sericata*.

Despite the progress made in recent years in the development of debridement compositions, it would still be desirable to provide clearly defined debridement compounds or compositions comprising defined components with at least similar if not improved properties as compared to the above discussed prior art materials. This aim could e.g. be achieved by identifying the active principle responsible for improved wound healing provided by maggots. Such compounds would also be useful for cosmetic applications.

Accordingly, in a first embodiment the invention relates to a nucleic acid molecule encoding
(i) a serine protease having the ability to cleave fibrin and casein, which is (a) a nucleic acid molecule encoding the serine protease comprising or consisting of the amino acid sequence of SEQ ID NO: 4; (b) a nucleic acid molecule comprising or consisting of the nucleotide sequence of SEQ ID NO: 3; (c) a nucleic acid molecule encoding a serine protease the amino acid sequence of which is at least 80% identical to the amino acid sequence of (a); preferably at least 85% identical, more preferably at least 90% identical, and most preferred at least 95% identical; (d) a nucleic acid molecule comprising or consisting of a nucleotide sequence which is at least 80% identical to the nucleotide sequence of (b), preferably at least 85% identical, more preferably at least 90% identical, and most preferred at least 95% identical; (e) a nucleic acid molecule which is degenerate with respect to the nucleic acid molecule of (d); or (f) a nucleic acid molecule corresponding to the nucleic acid molecule of any one of (a) to (d) wherein T is replaced by U;
(ii) a fragment of the serine protease of (i) with the same activity of the serine protease of (i);
(iii) a propeptide of the serine protease of (i) which is cleaved to its active form preferably immediately before or during treatment of a wound, wherein the propeptide is encoded by a nucleic acid molecule selected from (a) a nucleic acid molecule encoding the serine protease propeptide comprising or consisting of the amino acid sequence of SEQ ID NO: 6; (b) a nucleic acid molecule comprising or consisting of the nucleotide sequence of SEQ ID NO: 5; (c) a nucleic acid molecule encoding a serine protease propeptide the amino acid sequence of which is at least 80% identical to the amino acid sequence of (a); preferably at least 85% identical, more preferably at least 90% identical, and most preferred at least 95% identical; (d) a nucleic acid molecule comprising or consisting of a nucleotide sequence which is at least 80% identical to the nucleotide sequence of (b), preferably at least 85% identical, more preferably at least 90% identical, and most preferred at least 95% identical; (e) a nucleic acid molecule which is degenerate with respect to the nucleic acid molecule of (d); or (f) a nucleic acid molecule corresponding to the nucleic acid molecule of any one of (a) to (d) wherein T is replaced by U; or (iv) a pre-propeptide of the serine protease of (i), wherein the pre-propeptide is encoded by a nucleic acid molecule selected from (a) a nucleic acid molecule encoding the serine protease pre-propeptide comprising or consisting of the amino acid sequence of SEQ ID NO: 2; (b) a nucleic acid molecule comprising or consisting of the nucleotide sequence of SEQ ID NO: 1; (c) a nucleic acid molecule encoding a serine protease pre-propeptide the amino acid sequence of which is at least 80% identical to the amino acid sequence of (a); preferably at least 85% identical, more preferably at least 90% identical, and most preferred at least 95% identical; (d) a nucleic acid molecule comprising or consisting of a nucleotide sequence which is at least 80% identical to the nucleotide sequence of (b), preferably at least 85% identical, more preferably at least 90% identical, and most preferred at least 95% identical; (e) a nucleic acid molecule which is degenerate with respect to the nucleic acid molecule of (d); or (f) a nucleic acid molecule corresponding to the nucleic acid molecule of any one of (a) to (d) wherein T is replaced by U.

The term "nucleic acid molecule" in accordance with the present invention includes DNA, such as cDNA or genomic DNA, and RNA. Further included are nucleic acid mimicking molecules known in the art such as synthetic or semi-synthetic derivatives of DNA or RNA and mixed polymers. Such nucleic acid mimicking molecules or nucleic acid derivatives according to the invention include phosphorothioate nucleic acid, phosphoramidate nucleic acid, 2'-O-methoxyethyl ribonucleic acid, morpholino nucleic acid, hexitol nucleic acid (HNA), peptide nucleic acid (PNA) and locked nucleic acid (LNA) (see Braasch and Corey, Chem Biol 2001, 8: 1). LNA is an RNA derivative in which the ribose ring is constrained by a methylene linkage between the 2'-oxygen and the 4'-carbon.

The term "serin protease" characterizes proteins having proteolytic activity as belonging to a subgroup the members of which comprise a serine in their active centre which together with histidine and aspartate forms the catalytic triad common to most serine proteases (Rawlings, N. D., Barrett, A. J. (1994). Families of serine peptidases. *Meth. Enzymol.* 244:19-61). Serine-proteases are classified as hydrolases and belong to the EC numerical classification scheme subgroup 3.4.21. The proteins encoded by the nucleic acid molecule of the invention may either themselves exhibit the proteolytic activity of a serine protease (e.g. SEQ ID NO: 4) or after further maturation or activation (e.g. SEQ ID NO: 2 or 6), e.g. by proteolytical processing; see also the discussion of the propeptide of the invention below. Proteolytical processing may include the cut-off of a signal peptide from a pre-propeptide (e.g. the pre-propeptide having SEQ ID NO: 2) and the further proteolytical processing of the propeptide (e.g. the propeptide having SEQ ID NO: 6) by proteolytic cleavage.

The term "signal peptide" as used herein defines a short amino acid sequence (preferably, 3-60 amino acids long) that directs the transport of a protein to a particular cell compartment and preferably to the endoplasmic reticulum.

The term "propeptide" as used herein describes a linear molecular chain of amino acids, which is a precursor of a protein and is cleaved during maturation or activation of the protein (e.g. the amino acid sequence of SEQ ID NO: 6 or a amino acid sequence encoded by the nucleotide sequence of SEQ ID NO: 5). The term "pre-propeptide" as used herein is a precursor of the propeptide and further includes a signal peptide (e.g. amino acid sequence of SEQ ID NO: 2 or an amino acid sequence encoded by the nucleotide sequence of SEQ ID NO: 1). It is the primary translation product. Also if the pre-propeptide is applied to a wound, it is cleaved to its active form preferably immediately before or during treatment of said wound.

The term "having the ability to cleave fibrin and casein" preferably only refers to the activity of the mature protein but may also include the pending activity (to be achieved by the mentioned cleavage(s)) of the pre-propeptide and the propeptide which are precursors of the mature protein.

The term "protein" as used herein interchangeably with the term "polypeptide" or "peptide" describes linear molecular chains of amino acids, including single chain proteins or their fragments, preferably containing more than 30 amino acids. An amino acid stretch of 30 amino acids and less than 30 amino acids would normally only be called peptide but not a polypeptide. Depending on the circumstances, the term "protein" or "polypeptide" herein may denote the mature protein (e.g. the amino acid sequence of SEQ ID NO: 4 or a amino acid sequence encoded by the nucleotide sequence of SEQ ID NO: 3), the propeptide (e.g. the amino acid sequence of SEQ ID NO: 6 or a amino acid sequence encoded by the nucleotide sequence of SEQ ID NO: 5) or the pre-propeptide (e.g. the amino acid sequence of SEQ ID NO: 2 or a amino acid sequence encoded by the nucleotide sequence of SEQ ID NO: 1). Polypeptides may further form oligomers consisting of at least two identical or different molecules. The corresponding higher order structures of such multimers are, correspondingly, termed homo- or heterodimers, homo- or heterotrimers etc. Furthermore, peptidomimetics of such proteins/polypeptides where amino acid(s) and/or peptide bond(s) have been replaced by functional analogues are also encompassed by the invention. Such functional analogues include all known amino acids other than the 20 gene-encoded amino acids, such as selenocysteine. The terms "polypeptide", "protein" and "peptide" also refer to naturally modified polypeptides/proteins and peptides where the modification is effected e.g. by glycosylation, acetylation, phosphorylation and similar modifications which are well known in the art.

In connection with the fragments of the present invention, the term "the same activity" refers to the biological activities as listed herein which are present in fragments of the serine protease debrilase according to the invention. Fragments according to this embodiment of the present invention can be polypeptides or peptides of equal or less than 30 amino acids, depending on their length.

In accordance with the present invention, the term "percent (%) sequence identity" describes the number of matches ("hits") of identical nucleotides/amino acids of two or more aligned nucleic acid or amino acid sequences as compared to the number of nucleotides or amino acid residues making up the overall length of the template nucleic acid or amino acid sequences. In other terms, using an alignment, for two or more sequences or subsequences the percentage of amino acid residues or nucleotides that are the same (e.g. 80%, 85%, 90% or 95% identity) may be determined, when the (sub)sequences are compared and aligned for maximum correspondence over a window of comparison, or over a designated region as measured using a sequence comparison algorithm as known in the art, or when manually aligned and visually inspected. This definition also applies to the complement of a test sequence.

Amino acid sequence analysis and alignment in connection with the present invention was carried out using the NCBI BLAST algorithm (Stephen F. Altschul, Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402). The skilled person is also aware of suitable programs to align nucleic acid sequences.

Substitutions in the amino acid sequence of the serine protease of the present invention as compared to SEQ ID NOs: 2, 4 or 6 are preferably conservative. This means that substitutions preferably take place within one class of amino acids. For example, a positively charged amino acid is preferably mutated to another positively charged amino acid. The same holds true for the classes of basic, aromatic or aliphatic amino acids.

The term "degenerate" in accordance with the present invention refers to the degeneracy of the genetic code. Degeneracy results because a triplet code designates 20 amino acids and a stop codon. Because four bases exist which are utilized to encode genetic information, triplet codons are required to produce at least 21 different codes. The possible $4^3$ possibilities for bases in triplets give 64 possible codons, meaning that some degeneracy must exist. As a result, some amino acids are encoded by more than one triplet, i.e. by up to six. The degeneracy mostly arises from alterations in the third position in a triplet. This means that nucleic acid molecules having a different sequence than that specified above, but still encoding the same polypeptide lie within the scope of the present invention.

The problem often encountered when wounds do not heal in an appropriate time is the removal of "fibrin cuffs" and necrotic tissue to enable infiltration of fibroblasts and therefore the onset of the wound healing process. The present inventors have surprisingly found that the serine protease encoded by the nucleic acid of the present invention has excellent properties to prepare the wound for natural healing by dissolving these fibrin cuffs. It is a biologically active serine protease which is believed to be the major active principle of the wound healing activity of Lucilia sericata. The enzyme is also referred to herein as "debrilase", referring to its suggested use for the debridement of wounds.

The larvae of Lucilia sericata are generally used in clinical practice as living organisms to treat wounds which are resistant to conventional treatment. Since the maggot therapy is rather unpleasant to many patients and the secretions of the insects are far from being a defined pharmaceutical composition the present inventors set out to identify at least one of the active principles of wound debridement by a molecular approach.

The generation of a cDNA-library from mRNA (the transcriptome) of second instar larvae fed on blood agar led to the identification of a nucleic acid encoding a trypsin-like protease and the corresponding amino acid sequence expressed with high abundance which is likely to be the major protease involved in wound debridement by larvae of Lucilia sericata. The enzyme was not found in cDNA libraries derived from mRNA isolated from 5 days old larvae (third instar). This corresponds to the decrease of debriding activity with increasing larval stages (Chambers et al. 2003).

The screening of said libraries for proteolytic activity on casein yielded several cDNA sequences encoding proteases in the transcriptome of second instar larvae induced by blood-substrate. Analysis of cDNA-sequences in the library of induced second instar larvae led to the identification of proteases only present in the cDNA library generated from second instar larvae but not in the transcriptome of larvae in the later stage (third instar). Some of the proteases found exhibited nucleic acid sequence similarity to phosphochymotrypsin, trypsin or chymotrypsin, respectively. No metallo-, threonine-, cysteine-, aspartic acid- or glutamic acid type proteases were found.

In a first agar plate screening on skim milk several cDNA clones were found to secrete enzymes with caseinoloytic activity but only one exhibited activity also on a fibrin containing substrate. This enzyme was characterised in detail by recombinant expression and assessment of its biochemical properties in different assays.

Nucleic acid sequence analysis revealed three serine-type proteases and two trypsin-type proteases with high abundance within the mRNA of induced larvae. The trypsin-type proteases revealed fibrinolytic and caseinolytic activity. Amino acid sequence analysis of one of the fibrinolytic proteases which corresponds to debrilase represented by amino acid sequence of SEQ ID NO. 4 and encoded by the nucleic acid sequence of SEQ ID NO: 2 showed a protein sequence identity of 76.1% to a trypsin-like protease from Sarcophaga sp. as closest similarity to known enzymes using NCBI BLAST algorithm (Stephen F. Altschul, Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402). Debrilase was found to be expressed with high abundance, thus it is likely to be the major protease involved in wound debridement by larvae of Lucilia sericata. Debrilase is expressed and translated as pre-propeptide including a signal peptide and propeptidic amino acids (FIG. 5A). The activation of the enzymatic activity is accomplished by cleaving-off the signal peptide and by further cleaving the propeptide thereby generating the mature protein (SEQ ID NO. 4) of debrilase, wherein the propeptide is apparently further cleaved by autoproteolysis. The mature protein is preferably encoded by the nucleic acid molecule consisting of SEQ ID NO. 3. The mature debrilase has the ability to cleave fibrin and casein. Its activity can be inhibited completely by PMSF (phenylmethanesulfonyl fluoride) and APMSF (4-amidinophenylmethanesulfonyl fluoride). No inhibition was detected using inhibitors for metallo-, threonine-, cysteine- or aspartic acid type proteases. This shows that the protein is a serine protease and has trypsin-like activity.

It is known that progressive wound conditions encompass a wide pH range (Greener B et al 2005. Proteases and pH in chronic wounds. J Wound Care; 14(2)). In another detailed study, 247 pH values in 39 patients with chronic wounds of varying origins were analysed over a period of 12 months, detecting values from 5.45 to 8.65 (Dissemond, J. et al., 2003, pH-Wert des Milieus chronischer Wunden, Untersuchungen im Rahmen einer modernen Wundtherapie, Der Hautarzt 54, No. 12, 959-965). Debrilase is highly stable and active in a pH range of 5-10 which makes it suitable in the application on chronic wounds exerting the wide pH range as described above.

Moreover, in a cellular receptor activation assay debrilase was found to have the ability to activate protease-activated receptor 2 (PAR 2). PAR 2 is a member of the large family of 7-transmembrane receptors that couple to guanosine-nucleotide-binding proteins. PAR 2 is also a member of the protease-activated receptor family. It is activated by trypsin, but not by thrombin. Trypsin accomplishes the proteolytic cleavage of the receptors extracellular amino terminus and the new amino terminus functions as a tethered ligand and activates the receptor. PAR 2 plays an important role in inflammation and pain, in fibroblast proliferation (Asano-Kato et al., Tryptase increases proliferative activity of human conjunctival fibroblasts through protease-activated receptor-2, Invest Ophthalmol Vis Sci., 2005 46(12):4622-6) and in formation of connective tissue contributing to wound healing (Borensztajn K. et al., 2008, Factor Xa stimulates proinflammatory and profibrotic responses in fibroblasts via protease-activated receptor-2 activation, 1: Am J Pathol. 172(2):309-20). Thus, the trypsin-like enzyme of the invention by cleaving the tethered ligand activates the receptor which then triggers biochemical processes involved in promoting wound healing. For example, it is envisaged that debrilase can be utilised advantageously for dissolving "fibrin cuffs" which are frequently observed on non-healing wounds, for removing necrotic tissue and for triggering a receptor mediated cascade of immune and cellular responses.

This is the first description and characterization after recombinant expression of a protease from Lucilia sericata with fibrinolytic, caseinolytic and PAR 2-activating activity and a wide pH-range of its enzymatic activity on the molecular level. It is envisioned that debrilase and fragments thereof with debrilase activity have the ability to prepare and pre-treat slow-healing or chronic wounds to make them susceptible for natural healing processes and/or conventional medical treatment by debriding the wound, i.e. removal of dead tissue and dissolution of fibrin cuffs. Furthermore, cosmetic used are envisaged which involve skin treatments to improve skin appearance or texture. Application of the propetide to a wound will lead to a conversion to the mature protein by enzymatic cleavage.

The present invention also relates to a vector comprising the nucleic acid molecule of the invention, i.e. a nucleic acid molecule encoding the mature protein, the propeptide or the pre-propeptide as described in the specification. In addition, the vector may contain a nucleic acid molecule encoding a fragment as described above.

A vector according to this invention is capable of directing the replication, and/or the expression of the nucleic acid molecule of the invention and/or the expression of the polypeptide encoded thereby.

Preferably, the vector is a plasmid, cosmid, virus, bacteriophage or another vector used conventionally e.g. in genetic engineering.

Exemplary plasmids and vectors are listed, for example, in Studier and coworkers (Studier, W. F.; Rosenberg A. H.; Dunn J. J.; Dubendroff J. W., 1990. Use of the T7 RNA polymerase to direct expression of cloned genes, Methods Enzymol. 185, 61-89) or the brochures supplied by the companies Novagen, Promega, New England Biolabs, Clontech and Gibco BRL. Other preferred plasmids and vectors can be found in: Glover, D. M., 1985, DNA cloning: a practical approach, Vol. I-III, IRL Press Ltd., Oxford; Rodriguez, R. L. and Denhardt, D. T. (eds), 1988, Vectors: a survey of molecular cloning vectors and their uses, 179-204, Butterworth, Stoneham; Goedeel, D. V., 1990, Systems for heterologous gene expression, Methods Enzymol. 185, 3-7; Sambrook, J.; Russell, D. W., 2001, Molecular cloning: a laboratory manual, $3^{rd}$ ed., Cold Spring Harbor Laboratory Press, New York.

Non-limiting examples of suitable vectors include prokaryotic plasmid vectors, such as the pUC-series, pBluescript (Stratagene), the pET-series of expression vectors (Novagen) or pCRTOPO (Invitrogen), lambda gt11, pJOE, the pBBR1-MCS series, pJB861, pBSMuL, pBC2, pUCPKS, pTACT1 and vectors compatible with expression in mammalian cells like pREP (Invitrogen), pCEP4 (Invitrogen), pMClneo (Stratagene), pXT1 (Stratagene), pSG5 (Stratagene), EBO-pSV2neo, pBPV-1, pdBPVMMTneo, pRS-Vgpt, pRSVneo, pSV2-dhfr, pIZD35, Okayama-Berg cDNA expression vector pcDV1 (Pharmacia), pRc/CMV, pcDNA1, pcDNA3 (Invitrogene), pSPORT1 (GIBCO BRL), pGEMHE (Promega), pLXIN, pSIR (Clontech), pIRES-EGFP (Clontech), pEAK-10 (Edge Biosystems) pTriEx-Hygro (Novagen) and pCINeo (Promega). Examples for plasmid vectors suitable for Pichia pastoris comprise e.g. the plasmids pAO815, pPIC9K and pPIC3.5K (all Invitrogen).

The nucleic acid molecule of the present invention referred to above may also be inserted into vectors such that a translational fusion with another nucleic acid molecule is generated. The products arising therefrom are termed fusion proteins and will be described further below. The other nucleic acid molecules may encode a protein which may e.g. increase the solubility and/or facilitate the purification of the protein encoded by the nucleic acid molecule of the invention. Non-limiting examples include pET32, pET41, pET43. The vectors may also contain an additional expressible nucleic acid coding for one or more chaperones to facilitate correct protein folding. Suitable bacterial expression hosts comprise e.g. strains derived from BL21 (such as BL21(DE3), BL21(DE3) PlysS, BL21(DE3)RIL, BL21(DE3)PRARE) or Rosettaa®.

Particularly preferred plasmids which can be used to introduce the nucleic acid encoding the serine protease of the invention into the host cell are: pUC18/19 (Roche Biochemicals), pKK-177-3H (Roche Biochemicals), pBTac2 (Roche Biochemicals), pKK223-3 (Amersham Pharmacia Biotech), pKK-233-3 (Stratagene) and pET (Novagen). Further suitable plasmids are listed in PCT/EP03/07148. Very particular preference is given to an expression system which is based on plasmids belonging to the pET series.

For vector modification techniques, see Sambrook and Russel, 2001. Generally, vectors can contain one or more origins of replication (ori) and inheritance systems for cloning or expression, one or more markers for selection in the host, e.g., antibiotic resistance, and one or more expression cassettes. Suitable origins of replication include, for example, the Col E1, the SV40 viral and the M13 origins of replication.

The coding sequences inserted in the vector can e.g. be synthesized by standard methods, or isolated from natural sources. Ligation of the coding sequences to transcriptional regulatory elements and/or to other amino acid encoding sequences can be carried out using established methods. Transcriptional regulatory elements (parts of an expression cassette) ensuring expression in prokaryotes or eukaryotic cells are well known to those skilled in the art. These elements comprise regulatory sequences ensuring the initiation of the transcription (e.g., translation initiation codon, promoters, enhancers, and/or insulators), internal ribosomal entry sites (IRES) (Owens et al., 2001) and optionally poly-A signals ensuring termination of transcription and stabilization of the transcript. Additional regulatory elements may include transcriptional as well as translational enhancers, and/or naturally-associated or heterologous promoter regions. Preferably, the nucleic acid molecule of the invention is operably linked to such expression control sequences allowing expression in prokaryotes or eukaryotic cells. The vector may further comprise nucleotide sequences encoding secretion signals as further regulatory elements. Such sequences are well known to the person skilled in the art. Furthermore, depending on the expression system used, leader sequences capable of directing the expressed polypeptide to a cellular compartment may be added to the coding sequence of the nucleic acid molecule of the invention. Such leader sequences are well known in the art. Specifically designed vectors allow the shuttling of DNA between different hosts, such as bacteria-fungal cells or bacteria-animal cells.

The nucleic acid molecules of the invention as described herein above may be designed for direct introduction or for introduction via liposomes, phage vectors or viral vectors (e.g. adenoviral, retroviral) into the cell. Additionally, baculoviral systems or systems based on Vaccinia Virus or Semliki Forest Virus can be used as vector in eukaryotic expression system for the nucleic acid molecules of the invention. Expression vectors derived from viruses such as retroviruses, vaccinia virus, adeno-associated virus, herpes viruses, or bovine papilloma virus, may be used for delivery of the nucleic acids or vector into targeted cell population. Methods which are well known to those skilled in the art can be used to construct recombinant viral vectors; see, for example, the techniques described in Sambrook, 2001 and Ausubel, 2001.

Promoters which are particularly advantageous for implementing the invention and which are to be used, in particular, in E. coli are known to the skilled person (Sambrook, J.; Fritsch, E. F. and Maniatis, T. (1989), Molecular cloning: a laboratory manual, 2nd ed., Cold Spring Harbor Laboratory Press, New York). Further suitable promoters are those selected from T7, lac, tac, trp, ara or rhamnose-inducible promoters. Other promoters are mentioned in (Cantrell, S A (2003) Vectors for the expression of recombinant proteins in E. coli. Methods in Molecular biology 235: 257-275; Sawers, G; Jarsch, M (1996) Alternative principles for the production of recombinant proteins in Escherichia coli. Applied Microbiology and Biotechnology 46(1): 1-9). Very particular preference is given to using the T7 promoter in the vector according to the invention (Studier, W. F.; Rosenberg A. H.; Dunn J. J.; Dubendroff J. W.; (1990), Use of the T7 RNA polymerase to direct expression of cloned genes, Methods Enzymol. 185, 61-89; or brochures supplied by the companies Novagen or Promega).

Examples for regulatory elements permitting expression in eukaryotic host cells are the AOX1 or GAL1 promoter in yeast or the CMV- (Cytomegalovirus), SV40-, RSV-promoter (Rous sarcoma virus), chicken beta-actin promoter, CAG-promoter (a combination of chicken beta-actin promoter and cytomegalovirus immediate-early enhancer), the gai10 promoter, human elongation factor 1α-promoter, CMV enhancer, CaM-kinase promoter, the Autographa californica multiple nuclear polyhedrosis virus (AcMNPV) polyhedral promoter or a globin intron in mammalian and other animal cells. Besides elements which are responsible for the initiation of transcription such regulatory elements may also comprise transcription termination signals, such as the SV40-poly-A site or the tk-poly-A site or the SV40, lacZ and AcMNPV polyhedral polyadenylation signals, downstream of the nucleic acid.

The co-transfection with a selectable marker such as kanamycin or ampicillin resistance genes for culturing in E. coli and other bacteria allows the identification and isolation of the transfected cells.

Selectable markers for mammalian cell culture are the dhfr, gpt, neomycin, hygromycin resistance genes. The transfected nucleic acid can also be amplified to express large amounts of the encoded (poly)peptide. The DHFR (dihydrofolate reductase) marker is useful to develop cell lines that carry several hundred or even several thousand copies of the gene of interest. Another useful selection marker is the enzyme glutamine synthase (GS) (Murphy et al. 1991; Bebbington et al. 1992).

Using such markers, the cells are grown in selective medium and the cells with the highest resistance are selected.

In a further embodiment, the present invention relates to a host cell transformed, transduced or transfected with the vector of the invention.

Host cells into which vectors containing the nucleic acid molecule of the invention can be cloned are used for replicating and isolating a sufficient quantity of the recombinant enzyme. The methods used for this purpose are well known to the skilled person (Sambrook, J.; Fritsch, E. F. and Maniatis, T. (1989), Molecular cloning: a laboratory manual, 2nd ed., Cold Spring Harbor Laboratory Press, New York).

Suitable prokaryotic host cells comprise e.g. bacteria of the species Escherichia, such as strains derived from E. coli BL21 (e.g. BL21(DE3), BL21(DE3)PlysS, BL21(DE3)RIL, BL21(DE3)PRARE, BL21 codon plus, BL21(DE3) codon plus), Rosetta®, XL1 Blue, NM522, JM101, JM109, JM105, RR1, DH5α, TOP 10, HB101 or MM294. Further suitable bacterial host cells are Streptomyces, Salmonella or Bacillus such as Bacillus subtilis. E. coli strains are preferred prokaryotic host cells in connection with the present invention.

Suitable eukaryotic host cells are e.g. yeasts such as Saccharomyces cerevisiae, Hansenula polymorpha or Pichia sp. such as P. pastoris, insect cells such as Drosophila S2 or Spodoptera Sf9 cells, or plant cells.

Very particular preference is given to an expression system which is present in E. coli BL21 as a procaryotic host and Pichia pastoris as a eucaryotic host.

Mammalian host cells that could be used include human Hela, HEK293, H9 and Jurkat cells, mouse NIH3T3 and C127 cells, COS1, COS 7 and CV1, quail QC1-3 cells, mouse L cells. Bowes melanoma cells and Chinese hamster ovary (CHO) cells.

The present invention furthermore relates to a method of producing a serine protease, a fragment, a propeptide or pre-propeptide thereof as described above comprising, culturing the host cell of the invention and isolating the serine protease, the fragment, the propeptide or the pre-propeptide produced.

Suitable conditions for culturing a prokaryotic or eukaryotic host are well known to the person skilled in the art. For example, suitable conditions for culturing bacteria are growing them under aeration in Luria Bertani (LB) medium. To increase the yield and the solubility of the expression product, the medium can be buffered or supplemented with suitable additives known to enhance or facilitate both. E. coli can be cultured from 4 to about 37° C., the exact temperature or sequence of temperatures depends on the molecule to be overexpressed. In general, the skilled person is also aware that these conditions may have to be adapted to the needs of the host and the requirements of the polypeptide expressed. In case an inducible promoter controls the nucleic acid of the invention in the vector present in the host cell, expression of the polypeptide can be induced by addition of an appropriate inducing agent. Suitable expression protocols and strategies are known to the skilled person.

Depending on the cell type and its specific requirements, mammalian cell culture can e.g. be carried out in RPMI or DMEM medium containing 10% (v/v) FCS, 2 mM L-glutamine and 100 U/ml penicillin/streptomycine. The cells can be kept at 37° C. in a 5% $CO_2$, water saturated atmosphere.

Suitable media for insect cell culture is e.g. TNM+10% FCS or SF900 medium. Insect cells are usually grown at 27° C. as adhesion or suspension culture. Suitable expression protocols for eukaryotic cells are well known to the skilled person and can be retrieved e.g. from in Sambrook, 2001.

Methods of isolation of the polypeptide produced are well-known in the art and comprise without limitation method steps such as ion exchange chromatography, gel filtration chromatography (size exclusion chromatography), affinity chromatography, high pressure liquid chromatography (HPLC), reversed phase HPLC, disc gel electrophoresis or immunoprecipitation, see, for example, in Sambrook, 2001.

The present invention further relates to a serine protease, fragment, propeptide, or pre-propeptide encoded by the nucleic acid molecule of the invention or produced by the method of the invention. As mentioned, this serine protease is also referred to as "debrilase".

As described above, the serine protease of the invention is characterized in that it (i) originates from *Lucilia sericata*, (ii) exhibits proteolytic activity against fibrin, casein and Tosyl-Gly-Pro-Arg-AMC, but not against Suc-Ala-Ala-Phe-AMC. (iii) The proteolytic activity of the serine protease of the invention against casein and fibrin is inhibited by the serine proteinase inhibitors PMSF and APMSF and (iv), debrilase preferably activates the protease-activated receptor PAR-2. It could surprisingly be shown that it is active in a wide pH range between pH 5 and 10 (see FIG. 3B).

As mentioned, the invention further relates to a propeptide of the serine protease of the invention which is cleaved to its active form preferably immediately before or during treatment of a wound. This propeptide preferably has the amino acid sequence of SEQ ID NO: 6 and also preferably is encoded by the nucleic acid sequence if SEQ ID NO: 5.

In a further embodiment, the present invention relates to a fusion protein comprising the serine protease of the invention, the fragment of the serine protease of the invention, the propeptide of the invention or the pre-propeptide of the invention.

In addition to the amino acid sequence of the serine protease (debrilase), the fragment, the propeptide or the pre-propeptide thereof of the present invention debrilase, a fusion protein according to the present invention contains at least one additional, heterologous amino acid sequence. Often, but not necessarily, these additional sequences will be located at the N- or C-terminal end of the polypeptide. It may e.g. be convenient to initially express the polypeptide as a fusion protein from which the additional amino acid residues can be removed, e.g. by a proteinase capable of specifically trimming the polypeptide of the present invention.

Exemplary fusion proteins of debrilase, a fragment thereof or the (pre-) propeptide of debrilase further comprise a peptide or protein which can function to mediate the adhesion of the fusion protein to a matrix contained in wound dressing in order to achieve a stable incorporation of debrilase into the medical article of the invention. The fusion protein can be selected from the group of surface active proteins or antibodies and fragments thereof. The properties of antibodies and fragments thereof will be described further below in connection with the antibody of the invention.

The present invention furthermore relates to a composition comprising the serine protease of the invention, the fragment of the serine protease or fragment thereof of the invention, the propeptide of the invention, the pre-propeptide of the invention, the fusion protein of the invention, the nucleic acid of the invention, the vector of the invention, the host cell of the invention, or combinations thereof.

In a preferred embodiment, the composition is a pharmaceutical composition.

In accordance with the present invention, the term "pharmaceutical composition" relates to a composition for administration to a patient, preferably a human patient. The pharmaceutical composition is preferably used in an adjuvant situation, i.e. for preparing the slow healing wound for natural healing processes or conventional medical treatment by removing necrotic tissue and dissolving fibrin cuffs (debridement). The pharmaceutical composition of the invention comprises the compounds recited above, alone or in combination. The composition may be in solid or liquid form and may be, inter alia, in the form of (a) powder(s), (a) solution(s) or (an) aerosol(s), cream(s), ointment(s) or gel(s). The pharmaceutical composition of the present invention may, optionally and additionally, comprise a pharmaceutically acceptable carrier. By "pharmaceutically acceptable carrier" is meant a non-toxic solid, semisolid or liquid filler, diluent, encapsulating material or formulation auxiliary of any type. Examples of suitable pharmaceutical carriers are well known in the art. Compositions comprising such carriers can be formulated by well known conventional methods. The pharmaceutical composition can be administered topically. The dosage regimen corresponding to a suitable dose for administration will be determined by the attending physician and clinical factors which may, inter alia, depend on the size of the wound, the stage or severity of its condition. The concentration of the compound(s) as recited above in a composition for topical application can be in the range of 0.001 to 1% (w/w), preferably 0.01-0.1% (w/w). Topical application on wounds is preferably repeated in one or more than one daily applications.

The compound(s) as recited above can be used as active ingredient in pharmaceutical composition for the debridement of chronic and slow-healing wounds by dissolution of the fibrin cuff. The pharmaceutical composition according to the invention is preferably used in an adjuvant situation, i.e. for preparing the slow healing wound for natural healing processes or conventional medical treatment by removing necrotic tissue and dissolving fibrin cuffs (debridement).

The pharmaceutical composition of the invention can be applied in combination with (solid) carriers or matrices such as dressing(s), band aid(s) or tape(s). The compound(s) can be covalently or non-covalently bound to said carrier or matrix. These can be applied to wounds to promote wound healing.

For example, the compound(s) may be incorporated into a dressing to be applied over the wound. Examples of such dressings include staged or layered dressings incorporating slow-release hydrocolloid particles containing the wound healing material or sponges containing the wound healing material optionally covered by conventional dressings. The concentration of a solution of the pharmaceutical composition to be immobilised in a matrix of a wound dressing is generally in the range of 0.001 to 1% (w/v) preferably 0.01-0.1% (w/v). Furthermore, the compound(s) as recited above can be incorporated into a suitable material capable of delivering the enzyme to a wound in a slow release or controlled release manner.

Renewal of the wound dressing in appropriate intervals (e.g. 24 h) should be repeated until complete removal of fibrin cuff and necrotic tissue is accomplished. The dressing is suitable for any wound comprising necrotic tissue including leg ulcers, pressure sores, diabetic foot ulcers and burns. Preferably, the dressing comprises a layer of absorbent material such as hydrocolloids, foam, e.g. polyurethane foam, alginates, chitosan, so it may be used on exudating wounds whilst protecting the surrounding skin from maceration. The wound-contacting layer can be coated with an excipient, e.g. petrolatum, to prevent the dressing from sticking to the wound. The compound(s) according to the invention may be incorporated in a polymeric material such as e.g. cellulose, polylactates, polyvinyls, acrylic copolymers and may be integrated in the dressing in different ways. In one embodiment the polymeric material is in the form of a film on the wound-facing surface of the dressing. A high concentration of the compound(s) is desired on the surface of the dressing contacting the wound bed in order to obtain a more effective debridement due to a high initial release of the enzyme. The film may be in the form of a layer or it may be coated on a net.

Especially in the case of third degree burns, band aids comprising debrilase as debriding enzyme can be used in a wound debridement therapy.

In a formulation comprising the above compound(s), optionally comprised in a sterile carrier, the pharmaceutical composition of the invention in liquid form can be sprinkled over the wound area or, in solid or in liquid form, be incorporated into a carrier to be applied to the wound.

In a preferred embodiment, the serine protease of the invention is comprised in a solid carrier such as a wound dressing or tape in its inactive form and may be activated through cleavage of a (pre-)propeptide as described above by different means e.g. when brought in contact with wound exudate. It is preferred that the enzyme activity lasts during the recommended wear time of the dressing, depending on the amount of exudate.

A gel formulation of the pharmaceutical composition of the present invention further comprises at least one gel forming agent commonly used in pharmaceutical gel formulations. Examples of gel forming agents are cellulose derivatives such as methyl cellulose, hydroxyethyl cellulose, and carboxymethyl cellulose; vinyl polymers such as polyvinyl alcohols, polyvinyl pyrrolidones; and carboxypoly-methylene derivatives such as carbopol. Further gelling agents that can be used for the present invention are pectins, gums, alginates, agar and gelatine. Furthermore, the gel or emugel formulation may contain auxiliary agents commonly used in this kind of formulations such as preservatives, antioxidants, stabilizers, colorants and perfumes.

In another preferred embodiment, the composition is a cosmetic composition.

A cosmetic composition according to the invention is for use in non-therapeutic applications.

Cosmetic compositions may also be defined by their intended use, as compositions intended to be rubbed, poured, sprinkled, or sprayed on, or otherwise applied to the human body for cleansing, beautifying, promoting attractiveness, or altering the appearance.

The particular formulation of the cosmetic composition according to the invention is not limited. Envisaged formulations include rinse solutions, emulsions, creams, milks, gels such as hydrogels, ointments, suspensions, dispersions, powders, solid sticks, foams, sprays and shampoos. For this purpose, the cosmetic composition according to the invention may further comprise cosmetically acceptable diluents and/or carriers. Choosing appropriate carriers and diluents in dependency of the desired formulation is within the skills of the skilled person. Suitable cosmetically acceptable diluents and carriers are well known in the art and include agents referred to in Bushell et al. (WO 2006/053613). Preferred formulations for said cosmetic composition are rinse solutions and creams.

The application of the composition of the invention in cosmetics is aiming at treating the skin enzymatically for peeling and smoothening and/or intervention with scar formation. A suitable concentration of the compound(s) of the invention for cosmetic use is believed to be in the range of 0.0001 to 1% (w/v), preferably 0.0001 to 0, 1% (w/v), even more preferably 0.001 to 0.1% (w/v).

Preferred amounts of the cosmetic compositions according to the invention to be applied in a single application are between 0.1 and 10 g, more preferred between 0.1 and 1 g, most preferred 0.5 g. The amount to be applied also depends on the size of the area to be treated and has to be adapted thereto.

In another aspect, the present invention relates to the serine protease of the invention, the fragment of the serine protease of the invention, the propeptide of the invention, the pre-propeptide of the invention, the fusion protein of the invention, the nucleic acid of the invention, the vector of the invention or the host cell of the invention for the preparation of a cosmetic composition for skin peeling, skin smoothening or the intervention with scar formation, most preferably in the form of an adjuvant therapy. The invention furthermore relates to the serine protease of the invention, the fragment of the serine protease of the invention, the propeptide of the invention, the pre-propeptide of the invention, the fusion protein of the invention, the nucleic acid of the invention, the vector of the invention or the host cell of the invention for use in the treatment of wounds.

The particulars of the composition comprising the compound(s) of the invention to be used in connection with the above applications in cosmetics and therapeutics have been described above.

In a preferred embodiment, the wounds are chronic or slow healing wounds.

In a further aspect, the invention relates to a method for treating a wound to promote healing thereof in a human or non-human mammal which comprises applying to the wound a therapeutically effective amount of a sterile composition comprising the serine protease, fragment thereof, the propeptide, the pre-propeptide, the fusion protein, the nucleic acid, the vector or the host cell according to the invention as active ingredient. The invention also relates to the use of a compound of the invention as recited above in the preparation or manufacture of a medical article like a band aid, dressing or tape for the debridement of wounds and dissolution of the fibrin cuff.

The invention furthermore relates to the serine protease of the invention, the fragment of the serine protease of the invention, the propeptide of the invention, the pre-propeptide of the invention, the fusion protein of the invention, the nucleic acid of the invention, the vector of the invention or the host cell of the invention for use in the treatment of skin diseases accompanied by skin lesions and/or impaired wound healing. Examples of such skin lesions and/or impaired healing are psoriasis, atopical dermatitis, contact dermatitis and eczema and urticaria.

In a preferred embodiment, the composition of the invention additionally comprises at least one component selected from the group of a further protease, nuclease, excipient, anti-microbial agent and pain-relieving agent.

The debridement process as well as dressing changes may give rise to pain for the patient, and thus it may be preferred to incorporate a pain-relieving agent such as an analgesic or an anaesthetic compound in the dressing of the present invention.

The dressing of the present invention may further comprise debriding compositions other than enzymes, which may have additive or synergistic debriding effect. An example of such a compound may be urea.

The invention also relates to an antibody or fragment or derivative thereof specifically binding to the serine protease of the invention, or a fragment thereof or the propeptide or pre-propeptide of the serine protease of the invention.

An antibody according to the present invention specifically binds to the serine protease (debrilase) as described in detail herein above or fragments thereof having the activity of debrilase as described above or the propeptide or pre-propeptide of the serine protease of the present invention.

The antibody of the present invention can be, for example, polyclonal or monoclonal. The term "antibody" also comprises derivatives or fragments thereof which still retain the binding specificity. Such fragments comprise, inter alia, Fab fragments, F(ab')$_2$, Fv fragments or scFv derivatives. Techniques for the production of antibodies and fragments thereof are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1998. These antibodies can be used, for example, for immunoprecipitation or affinity purification of debrilase or fragments thereof.

The antibody of the invention also includes embodiments such as chimeric, single chain and humanized antibodies. Various procedures are known in the art and may be used for the production of such antibodies and/or fragments. Further, techniques described for the production of single chain antibodies can be adapted to produce single chain antibodies specific for debrilase or fragments thereof etc. described above. Also, transgenic animals may be used to express humanized antibodies specific for debrilase or fragments thereof. Most preferably, the antibody of this invention is a monoclonal antibody. For the preparation of monoclonal antibodies, any technique that provides antibodies produced by continuous cell line cultures can be used. Examples for such techniques include the hybridoma technique (Köhler and Milstein Nature 256 (1975), 495-497), the trioma technique, the human B-cell hybridoma technique (Kozbor, Immunology Today 4 (1983), 72) and the EBV-hybridoma technique to produce human monoclonal antibodies (Cole et al., Monoclonal Antibodies and Cancer Therapy, Alan R. Liss, Inc. (1985), 77-96). Surface plasmon resonance as employed in the BIAcore system can be used to increase the efficiency of phage antibodies which bind to an epitope of the compounds described above (Schier, Human Antibodies Hybridomas 7 (1996), 97-105; Malmborg, J. Immunol. Methods 183 (1995), 7-13). It is also envisaged in the context of this invention that the term "antibody" comprises antibody constructs that may be expressed in cells, e.g. antibody constructs which may be transfected and/or transduced via, amongst others, viruses or plasmid vectors. Once the antibody according to the present invention has been obtained, the antibody itself or the DNA encoding it can be sequenced providing for the information to recombinantly produce the antibody of the invention in small or large scale. Methods of the production of a recombinant antibody are known to the person skilled in the art.

The term "specifically binds", interchangeably used with "specifically interacts with", in accordance with the present invention means that the antibody does not or essentially does not cross-react with an epitope of similar structure. Cross-reactivity of a panel of antibodies under investigation may be tested, for example, by assessing binding of said panel of antibodies under conventional conditions to the epitope of interest as well as to a number of more or less (structurally and/or functionally) closely related epitopes. Only those antibodies that bind to the epitope of interest in its relevant context (e.g. a specific motif in the structure of a protein) but do not or do not essentially bind to any of the other epitopes are considered specific for the epitope of interest and thus to be antibodies in accordance with this invention. Corresponding methods are described e.g. in Harlow and Lane, 1988 and 1999, loc cit.

The invention is herein described, by way of example only, with reference to the accompanying drawings for purposes of illustrative description of the preferred embodiments of the present invention.

The figures show:

FIG. 1: Diffusion assay on agar containing casein showing a clearing zone around a debrilase secreting clone of *E. coli*.

FIG. 2: Activity assay in agar containing fibrin showing a clearing zone around debrilase active sample A) debrilase positive clone growing on fibrin containing substrate, B) agar diffusion assay with crude extracts from a debrilase-positive recombinant *E. coli* clone: (a) undiluted crude extract b) 1:10 dilution in PBS c) 1:50 dilution in PBS.

FIG. 3: A) enzyme assay for identifying the activity profile of recombinant debrilase by use of known serine protease (PMSF) and trypsin like serine protease (APMSF) inhibitors; B) activity assay with debrilase in puffers of different pH-values to identify the pH-profile of recombinant debrilase.

Figure 4:
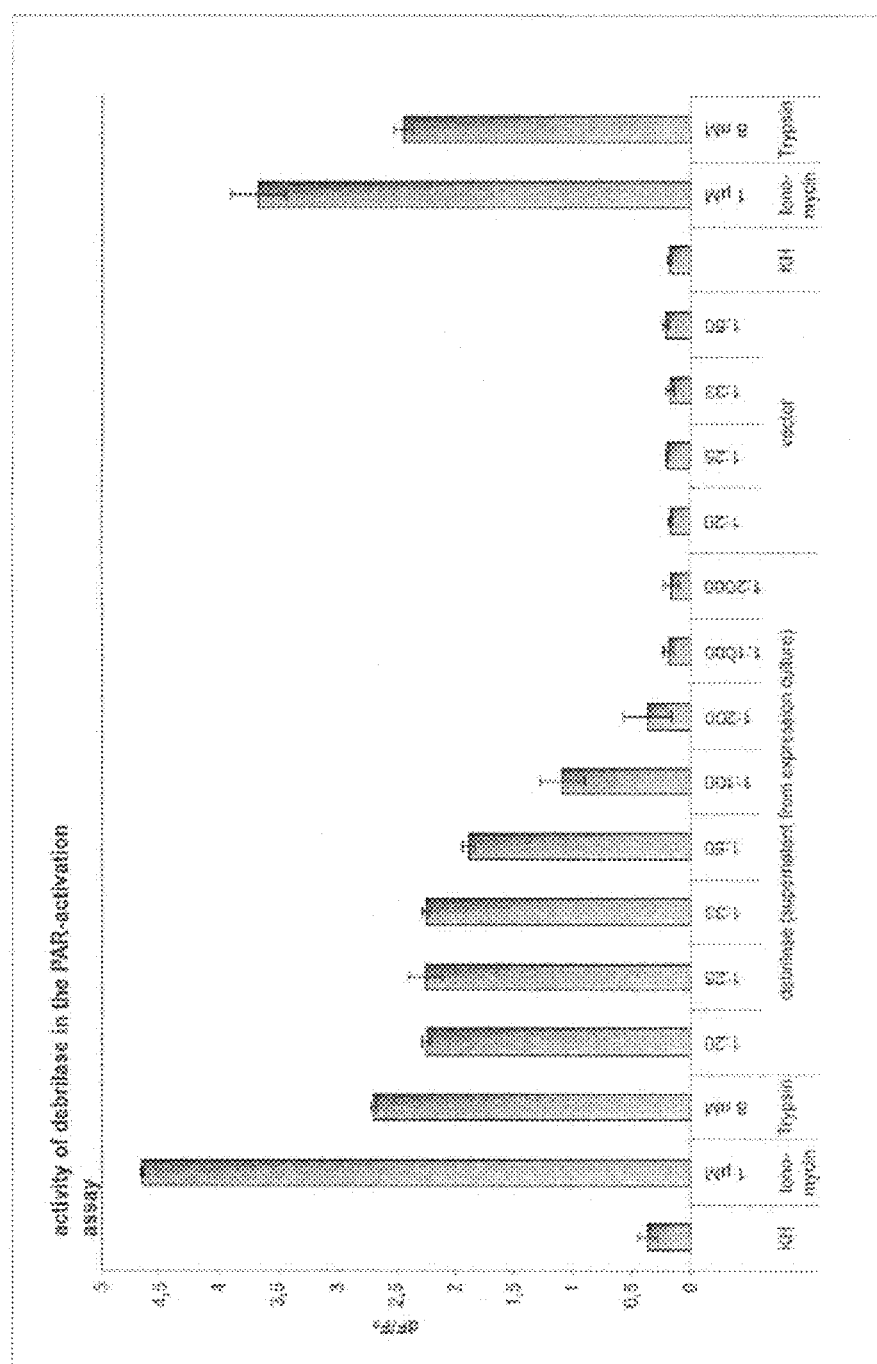

FIG. 4: Activation of PAR 2 in a cell based receptor assay with HEK232 cells with $Ca^{2+}$-flux as read-out.

FIG. 5: Alignment of the pre-propeptide amino acid of debrilase (A) (SEQ. ID. NO:2) and cDNA nucleotide sequence (B) (SEQ. ID. NO:1) with the nearest neighbour sequence being the trypsin like protein from *Sarcophaga bullata* (SEQ. ID. NOs:9 and 10) showing 76% identity for nucleotide and protein sequence using NCBI BLAST algorithm. (A) The signal peptide of debrilase consists of amino acids 1 to 16 (the signal peptide is shown bold), the propeptide consists of amino acids 17 to 254 (propeptidic amino acids 17 to 26 are underlined) and the proteolitically processed mature polypeptide of debrilase consists of amino acids 27 to 254.

Figure 6:
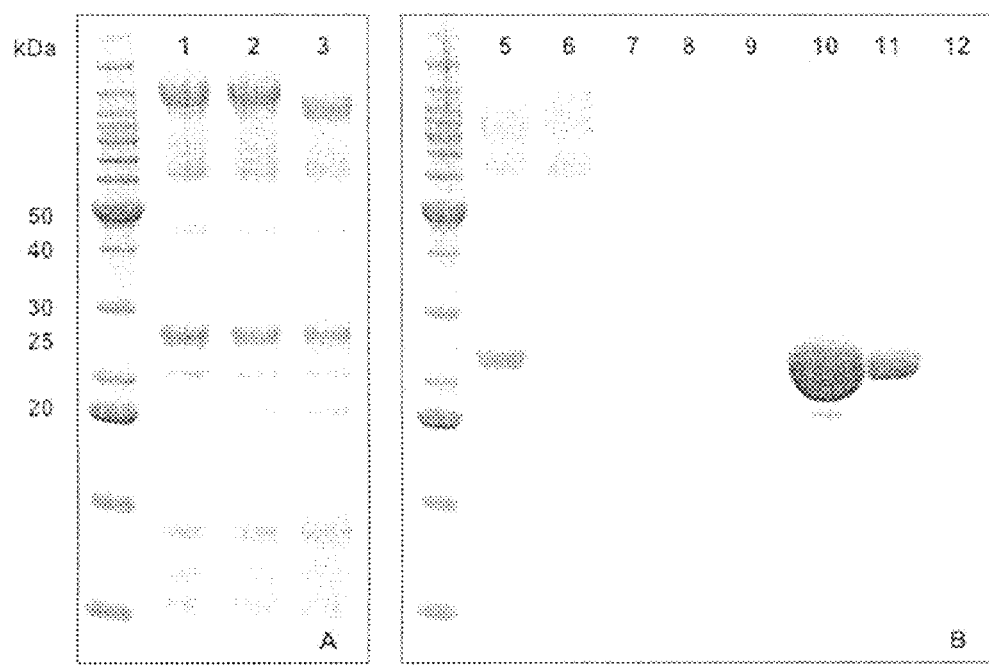

FIG. 6: (A) SDS PAGE of culture supernatant: 1) after centrifugation; 2) pre-filtration [0.45 μm]; 3) sterile filtration [0.22 μm], MW of the propeptide 25.7 kDa. (B) Visualisation of activated mature Debrilase; 5) after dialysis and subsequent pH shift from 5.5 to 8; 6) affinity chromatography column flow-through (unbound protein); 7) wash flow through, (8 to 12) fractionated elution 1 to 5, respectively (molecular weight of the mature protein 24.6 kDa).

The examples illustrate the invention.

EXAMPLES

General Methods and Materials

Isolation of mRNA of Different Larval Stases from *Lucilia sericata*

2 days old maggots from the green bottlefly (*Lucilia sericata*) were purchased from BioMonde (BioMonde, 22885 Barsbüttel, Germany). Isolation of total RNA was done after feeding for 24 hours (second instar stage) on blood-agar (1.5% (w/v) agar containing 10% bovine blood) to enhance production of proteases and after 3 days when the production of enzymes is markedly decreased in the third instar stage (Chambers et al. 2000, Degradation of extracellular matrix components by defined proteinases from the greenbottle larva *Lucilia sericata* used for the clinical debridement of non-healing wounds, Brit J Dermatol. 148: 14-23). For isolation of total-RNA 3 larvae (ca. 30 mg) were shock frozen with liquid nitrogen and pulverised mechanically. RNA was isolated using the kit "Total RNA Isolation, NucleoSpin RNA II" (purchased from Macherey-Nagel, 52313 Duren, Germany) yielding 47 μg total RNA.

Generation of an *E. coli* cDNA Library from Total RNA Isolated from Larvae of *Lucilia sericata*

The generation of a cDNA-library from said *Lucilia sericata* RNA was accomplished according to the "SMART cDNA Library Construction Kit User Manual" (CLONTECH Laboratories, Inc.). In vitro packaging of the final ligation reaction and subsequent transformation in *E. coli* XL-1 Blue resulted in 1.5×10E6 primary plaque forming units.

Primary phages were harvested and stored in phage stabilization buffer containing 7% DMSO at −80° C. for subsequent infection and mass excision in *E. coli*.

Conversion of the lambda phage library into the corresponding plasmid library was performed by "Cre" recombinase-mediated mass excision of the phage embedded plasmids according to the "SMART cDNA Library Construction Kit User Manual" (CLONTECH Laboratories, Inc.).

Heterogeneity and Quality of the Library was Tested by Restriction Analysis

Identification of Proteases from Lydiai Sericata cDNA-Library

Colony forming units resulted from mass excision described above were screened on agar media containing 2% skim milk under selective conditions. Expression of heterologous proteases was driven by the vector comprising inducible $P_{lac}$ promoter. Colonies expressing heterologous proteases were detected by the formation of clearing zones in the turbid Skim Milk medium around the colonies.

Isolation and Purification of Debrilase Protein from *E. Coli* Culture Expression Culture In order to obtain enzyme samples of the debrilase containing sufficient enzymatic activity for a characterisation of the enzyme either the cDNA clone expressing the corresponding protease or a more suited expression construct set up in a typical expression vector like e.g the pET26b-vector (Novagen) and a suitable expression host like e.g. *E. coli* Rosetta (DE3) (Novagen) were used. For the construction of the expression constructs, the corresponding debrilase genes were PCR amplified to introduce unique restriction enzyme recognition sequences upstream and downstream of the open reading frame (ORF) which allowed to ligate the genes encoding the protease with the expression vector e.g. pET26b in a definite way. The restriction enzyme recognition sequences were chosen on the basis of their absence in the coding region of the debrilase gene and could be e.g. NdeI, HindIII, EcoRI, XhoI. The absence of unwanted second site mutations due to erroneous amplification by the polymerase was confirmed by sequencing of the cloned amplicon.

The cDNA clones or the expression constructs were used to inoculate e.g. 200 ml of culture medium complemented with the appropriate antibiotic in a 1 l Erlenmayer flask. LB-medium and antibiotics in the following concentration were used: 100 µg/ml ampicillin, 25 µg/ml kanamycin, chloramphenicol 12.5 µg/ml. The initial optical density ($OD_{580}$) was adjusted to 0.05 and the cells grown at a temperature of 28° C. on a gyratory shaker. When the optical density reached the value of about 1 the expression from the lac-promoter of pTriplEx2 (Clontech) or from the T7-promoter of vectors from the pET-vector series e.g. pET26 was induced by addition of IPTG in the concentration of 20 µM-500 µM. Cells were harvested 4 to 20 h after induction by centrifugation. The cell sediment was resuspended in 5 ml 1×PBS, pH 7.0 and the cells disrupted by ultrasonication.

The molecular weight of debrilase is 27.4 kD for the complete protein including signal sequence, 25.7 for the hypothetical pro-peptide and 24.6 for the mature protein.

Solid Phase Activity Assay for Fibrinolytic Activity

To identify fibrinolytic activity in extracts of casein degrading clones a solid agar assay was used. For this, a solution A containing 200 mg agarose, 87 mg NaCl and 3 mg $CaCl_2$ were added to 10 ml 0.1 M Tris pH7.4 and incubated at 50° C. To a second solution B containing 10 ml 0.9% NaCl and 100 mg Fibrin (Sigma F3879), 20 µl Plasminogen (2 units/mg, Sigma P7397) e added and pre-incubated at 50° C. Both solutions were combined with 12 µl Thrombin (175-350 NIH units, Sigma T4265) and spread on agar plates using micro-well forming devices. In case of a fibrinolytic activity a clear zone appears in the opaque medium around extract containing cavities.

To identify fibrinolytic activity in casein degrading clones a solid agar assay was used. Therefore a medium A consisting of 10 ml 2× Luria Bertani containing 200 mg agarose, 87 mg NaCl and 3 mg $CaCl_2$ was incubated at 50° C. To a solution B containing 10 ml 0.9% NaCl and 100 mg Fibrin (Sigma F3879), 20 µl plasminogen (2 units/mg, Sigma P7397) was added and pre-incubated at 50° C. Both solutions were combined with 12 µl thrombin (175-350 NIH units, Sigma T4265) and appropriate antibiotics for selection and poured on agar plates under sterile conditions forming a opaque agar medium. In case of fibrinolytic activity expressed by heterologous clones a clear zone appears around the colony after over night incubation.

Liquid Phase Activity Assay and Inhibitory Profiling

Quantification of proteolytic activity was conducted by a fluorescence assay in 96-well plates with BODIPY-FL-Casein (Molecular Probes) used as substrate. Hereby, on the undigested substrate casein the labelling molecules are in close contact to each other and therefore fluorescence is suppressed by a quenching mechanism. In case of hydrolysis these molecules separate from each other and fluorescence can be excited at 485 nm and measured at 520 nm.

A standard assay contained 5 µg/ml BODIPY-FL-Casein in 100 µl PBS buffer and a series of dilutions of protease extract. Samples were incubated for 60 min at 37° C. and fluorescence was measured using a spectrophotometer (NovoStar, BMG LABTECH, Offenburg, Germany), applying the following parameters: excitation 485 nm, emission 520 nm, gain 5, one cycle, 10 flashes. Serine protease inhibitors APMSF (4-amidinophenylmethanesulfonyl fluoride) and PMSF (phenylmethanesulfonyl fluoride) were used for testing the specificity of the isolated protease. The following assay concentration were used:

| PMSF = serine protease inhibitor | 5 mmol/l |
|---|---|
| APMSF = trypsin like serine protease inhibitor | 1 mmol/l |

The Sequence Listing submitted herewith electronically is incorporated herein by reference.

The following examples are illustrative, but not limiting the scope of the present invention. Reasonable variations, such as those occur to the person skilled in the art, can be made herein without departing from the scope of the present invention.

*Pichia pastoris* Expression Culture

Heterologous expression of the serine protease of the invention, i.e. debrilase was carried out in the methylotrophic yeast *Pichia pastoris*, which is classified as a GRAS-organism by the Food and Drug Administration and is therefore established for pharmaceutical production processes. For expression an integrative vector system was used, providing a methanol inducible promoter. The native signal peptide of debrilase ("MFRFVALFAFVSCALA") (SEQ. ID. NO:7) was substituted by the vector encoded-factor signal sequence from *Saccharomyces cerevisiae* to facilitate efficient secretion in *Pichia*.

Fermentation was carried out in mineral medium with glycerol as sole carbon source in the first batch phase, fed batch mode was started after consumption of initial batch glycerol. Induction of heterologous expression was initiated by supplementation of methanol as inducer/carbon source and sorbitol as additional non-inhibiting feed during gene expression.

Stationary growth of the culture was reached after batch/fed-batch (FB) phase leading to an Optical Density of about 600. Induction was initiated by adding MeOH. To prevent heterologous enzyme from being activated autocatalytically at this point, process temperature was decreased from 30° C. to 20° C. Expression of debrilase was supported in the end phase of the process by feeding. Autocatalytic activation of the propeptide was achieved by increasing the pH of the culture medium from 5.5 to 6.8, during the purification procedure (see below).

Purification of Debrilase Protein from *Pichia pastoris* Culture Expression Culture Purification was carried out by affinity chromatography using serine protease inhibitor benzamidine coupled to sepharose carrier material (GE Healthcare). After removal of unbound protein purified the serine protease of the invention was harvested by competitive elution using buffer with addition of free benzamidine. SDS PAGE of the downstream procedure is visualized in FIG. 6. After subsequent dialysis against citrate storage buffer the purified protein was lyophilized and displayed as white dry powder.

N-Terminal Sequencing of Recombinantly Expressed Debrilase

For Edman sequencing the blot was fitted into the sample preparation cartridge. For determination of the amino acid sequence the protein sequencer Procise 492 (Applied Biosystems) was used. Reagents and protocols were applied as advised by the manufacturer. The resulting chromatograms were analysed using appropriate software (Applied Biosystems). Prior to each sample a standard sample and a blank were run.

Example 1

Screening for Proteases in an Expression Library Generated from *Lucilia sericata*

A phage library of 8×10E6 primary clones was screened for the expression of proteases. For this end, the phage library was transferred into a plasmid library by co-infection of *E. coli* with a f1 type helper phage according to the "SMART cDNA Library Construction Kit User Manual" (CLONTECH Laboratories, Inc.). The resulting colonies harbour the intrinsic plasmids excised from the phage vector.

The heterogeneity of the plasmid library was tested by isolation of forty plasmids from representative clones. In fact, every plasmid harboured an insert and these inserts showed complete diversity in size. In total, 3×10E5 cfu were screened on solid media containing 2% skim milk under selective conditions.

By isolation and sequencing of plasmid DNA from sixteen of these halo-forming colonies a pre-propeptide sequence of a protease with 76% identity on the amino acid level to a trypsin-like enzyme from *Sarcophaga bullata* was identified (SEQ ID NO: 2).

Example 2

Characterisation of a Fibrinolytic Protease

The identification of fibrinolytic activity was performed in agar plate assays described above. Colonies expressing fibrinolytic activity were identified by streaking out recombinant cells on nutrient agar containing turbid fibrin substrate. Cells harbouring plasmids with the identified protease showed clear zones around the colony after over night incubation at 37° C.

Fibrinolytic activity in cell free crude extracts was determined using buffered agar medium containing fibrin. Plates contained wells with a capacity of up to 200 µl which were formed using microplate devices during solification of the agar medium. Recombinant cells were sonicated and the resulting extract was centrifuged, places into the agar wells and incubated over night at 37° C. Crude extract with fibrinolytic activity was detected by a clear zone around microwells of the recombinant clone harbouring the protease gene of SEQ ID NO. 1.

Example 3

Profiling of a Fibrinolytic Protease

The recombinant protease type was identified in a liquid assay in a 96-well plate using inhibitors specific for different types of proteases. Herein, specific inhibitors for trypsin (4-amidinophenylmethyl-sulphonyl fluoride, APMSF), serine (phenylmethylsulphonyl fluoride, PMSF), aspartyl- (pepstatin A) and metallo-type proteases (1,10-phenanthroline) were measured. As shown in FIG. 3 A, the inhibitor-profile of the recombinant clone suggests a trypsin type activity, which corresponds to comparative amino acid sequence alignment data of SEQ ID NO: 2 with the BLAST data base, showing the closest homology being 76% to an enzyme from *Sarcophaga bullata* (FIG. 5).

Example 4

Stability at Different pH-Values

Activity of the debrilase was measured in liquid assay using appropriate buffer systems in the range of 3-10 (0.1 to 0.2 M citric acid buffer, pH 3-7; 0.05 M tris buffer, pH 8; 0.1 M carbonate buffer, pH 9-10) and the fluorogenic substrate Z-Gly-Gly-Arg-AMC. The release of 7-amino-4-methylcoumarin (AMC) was measured with a BMC Novostar Fluorometer ($\lambda_{excitation}$ 365 nm, $\lambda_{emission}$ 440 nm). The results are shown in FIG. 3 B. Debrilase exhibits enzymatic activity in a pH-range of 5-10 which corresponds to the similarly wide pH-range of the wound milieu.

Example 5

Activation of PAR 2 (Calcium Imaging)

The activity of debrilase as agonist of PAR 2 was monitored over time in a cell based fluorescence assay by use of a wild type HEK293 cell line endogenously expressing human PAR2. In brief, 1 day prior to performing the assay, HEK293 cells expressing human PAR2 were plated onto 96-well, black-walled, assay plates, at a density of 45,000 cells per well. Using a 96-well microplate reader (FlexStation®, Molecular Devices, Sunnyvale, Calif.), the change of the cellular calcium concentration was monitored by use of the calcium sensitive fluorescent dye fluo-4 (excitation 494 nm, emission 516 nm). The PAR 2 agonist trypsin (8 nM) was used as positive control. The dye-loaded cells in plates were placed into the fluorescence microplate reader to monitor fluorescence (excitation 488 nm, emission 520 nm) change after the addition of 50 µl assay buffer (118 mM NaCl; 4.7 mM KCl; 1.2 mM MgSO$_4$; 1.2 mM KH$_2$PO$_4$ 4.2 mM NaHCO$_2$; 1.3 mM CaCl$_2$; 10 mM HEPES (pH: 7.4)) supplemented with an agonist. Calcium mobilization was quantified as the change of peak fluorescence (ΔF) over the baseline level (F). Data were expressed as the mean S.E. of the ΔF/F value (=RFU, relative fluorescence units) of replicated independent samples. The analysis was done with the software of the FlexStation®.

Example 6

The Sequence of the First 10 Amino Acids of the Mature Debrilase

The aim of the example is to determine the sequence of the first 10 amino acids by N-terminal Edman sequencing. The sample (protein from FIG. 6 B, lane 5) was successfully sequenced from the N-terminus. The following major sequence was detected:

IVNGVDTTIQ (SEQ. ID. NO:8) which corresponds to the mature protein proposed by analysis of the primary sequence (FIG. 5A).

Example 7

Molecular and Enzymatic Properties of Debrilase

TABLE 1

Summary of molecular and enzymatic properties of Debrilase

| | |
|---|---|
| molecular weight: | 27.4 kDa (pre-pro-peptide), |
| | 25.7 kDa (pro-peptide), |
| | 24.6 kDa (mature protein) |
| $K_m$: | 0.07 mM* |
| $K_{cat}$: | 37.5 · s$^{-1}$ |
| specific activity: | 90 µmol* · min$^{-1}$ · mg$^{-1}$ enzyme |
| pH$_{opt}$: | 8 |
| T$_{opt}$: | 37° C. |

*measured in fluorometric assay using Z-Gly-Gly-Arg-AMC as substrate

---

The invention claimed is:

1. An isolated nucleic acid molecule encoding
   (i) a serine protease having the ability to cleave fibrin and casein, said serine protease encoded by
      (a) a nucleic acid molecule encoding the amino acid sequence of SEQ ID NO: 4;
      (b) a nucleic acid molecule comprising or consisting of the nucleotide sequence of SEQ ID NO: 3;
      (c) a nucleic acid molecule encoding the amino acid sequence which is at least 90% identical to the amino acid sequence of (a);
      (d) a nucleic acid molecule comprising or consisting of a nucleotide sequence at least 90% identical to the nucleotide sequence of (b);
      (e) a nucleic acid molecule which is degenerate with respect to the nucleic acid molecule of (d); or
      (f) a nucleic acid molecule corresponding to the nucleic acid molecule of any one of (a) to (d) wherein T is replaced by U.

2. A vector encoding the nucleic acid molecule of claim 1.

3. An isolated host cell transformed, transduced or transfected with the vector of claim 2.

4. A method of producing a serine protease comprising culturing the host cell of claim 3 and isolating the serine protease, the propeptide or the pre-propeptide produced.

5. A serine protease, propeptide, or pre-propeptide encoded by the nucleic acid molecule of claim 1 or produced by the method of claim 4.

6. A fusion protein comprising the serine protease, the propeptide, or the pre-propeptide of claim 5.

7. A composition comprising the nucleic acid of claim 1, the vector of claim 2, or the host cell of claim 3 or combinations thereof.

8. The composition of claim 7 which is a cosmetic composition.

9. The composition of claim 7 which is a pharmaceutical composition.

10. A method for treatment of skin peeling, skin smoothening or the intervention with scar formation, comprising contacting skin with the nucleic acid of claim 1, the vector of claim 2, or the host cell of claim 3.

11. A method for treatment of wounds, comprising contacting a wound with the nucleic acid of claim 1, the vector of claim 2, or the host cell of claim 3.

12. The method of claim 11 wherein the wounds are chronic or slow healing wounds.

13. A method for treatment of skin diseases accompanied by impaired wound healing comprising contacting a skin disease with the nucleic acid of claim 1, the vector of claim 2, or the host cell of claim 3.

14. The method claim 10, additionally comprising administering at least one component selected from the group of a further protease, nuclease, excipient, anti-microbial agent and pain-relieving agent.

15. The nucleic acid molecule of claim 1, wherein the nucleic acid encodes a propeptide of the serine protease of (i), and the propeptide is encoded by a nucleic acid molecule selected from:
   (a) a nucleic acid molecule encoding the amino acid sequence of SEQ ID NO: 6;
   (b) a nucleic acid molecule comprising or consisting of the nucleotide sequence of SEQ ID NO: 5;
   (c) a nucleic acid molecule encoding the amino acid sequence of which is at least 90% identical to the amino acid sequence of (a);
   (d) a nucleic acid molecule comprising or consisting of a nucleotide sequence which is at least 90% identical to the nucleotide sequence of (b);
   (e) a nucleic acid molecule which is degenerate with respect to the nucleic acid molecule of (d); or
   (f) a nucleic acid molecule corresponding to the nucleic acid molecule of any one of (a) to (d) wherein T is replaced by U.

16. The nucleic acid molecule of claim 1, wherein the nucleic acid encodes a pre-propeptide of the serine protease of (i), wherein the pre-propeptide is encoded by a nucleic acid molecule selected from
   (a) a nucleic acid molecule encoding the amino acid sequence of SEQ ID NO: 2;
   (b) a nucleic acid molecule comprising or consisting of the nucleotide sequence of SEQ ID NO: 1;
   (c) a nucleic acid molecule encoding the amino acid sequence which is at least 90% identical to the amino acid sequence of (a);
   (d) a nucleic acid molecule comprising or consisting of a nucleotide sequence at least 90% identical to the nucleotide sequence of (b);
   (e) a nucleic acid molecule which is degenerate with respect to the nucleic acid molecule of (d); or
   (f) a nucleic acid molecule corresponding to the nucleic acid molecule of any one of (a) to (d) wherein T is replaced by U.

17. The method of claim 11, additionally comprising administering at least one component selected from the group of a further protease, nuclease, excipient, anti-microbial agent and pain-relieving agent.

18. The method of claim 12, additionally comprising administering at least one component selected from the group of a further protease, nuclease, excipient, anti-microbial agent and pain-relieving agent.

* * * * *

SEQUENCE LISTING

<160> NUMBER OF SEQ ID NOS: 10

<210> SEQ ID NO 1
<211> LENGTH: 765
<212> TYPE: DNA
<213> ORGANISM: Lucilia sericata

<400> SEQUENCE: 1

```
atgttccggt ttgtagctct attcgctttc gttagctgtg ccttggcggg cgctattccc      60
aatgatttgg atggccgcat tgtcaatggt gtggatacca ccattcaggc ccatccctat     120
caggtttctt tgcaaaccaa caatggtttc catttctgcg gtggttccat catcagcgaa     180
gacattattg taactgctgc tcattgcatg caatcctaca aggcctacca attcaaagta     240
cgtttgggtt ccactgaata cgataatggt ggtgaattgg ttgccgtcaa gtcttttcaaa     300 taccacgaag gttacaatcc cgaaaccatg gttaatgatg ttgccgttat caaattagcc     360
actccagtgc gtgaatcttc caaggtacgt tatgttaaat tggctgagaa gacacctgct     420
actggcaccc cagctgtcgt tactggttgg ggttctaagt gcttcttgtt ctgccaaact     480
gcccctaaag ttttgcaaaa ggttgaggtc gatattgttg atgagaagac ctgcgcttcc     540
agcgaataca aatatggtga tgacatcaag gaaactatgt tgtgtgctta tgctgttaag     600
aaggatgctt gccaagtgta ttctggtggt cctttggttg ccaacaacaa attggtcggt     660
gttgtttcct ggggtaaagg ttgtgccctt gctggctatc ccggtgtata ctgcgatgtt     720
gctactgtcc gcagctggat tgaaaagact gccaagagtt tgtaa                     765
```

<210> SEQ ID NO 2
<211> LENGTH: 254
<212> TYPE: PRT
<213> ORGANISM: Lucilia sericata

<400> SEQUENCE: 2

```
Met Phe Arg Phe Val Ala Leu Phe Ala Phe Val Ser Cys Ala Leu Ala
 1               5                  10                  15

Gly Ala Ile Pro Asn Asp Leu Asp Gly Arg Ile Val Asn Gly Val Asp
            20                  25                  30
```

```
Thr Thr Ile Gln Ala His Pro Tyr Gln Val Ser Leu Gln Thr Asn Asn
        35                  40                  45

Gly Phe His Phe Cys Gly Gly Ser Ile Ile Ser Glu Asp Ile Ile Val
50                  55                  60

Thr Ala Ala His Cys Met Gln Ser Tyr Lys Ala Tyr Gln Phe Lys Val
65                  70                  75                  80

Arg Leu Gly Ser Thr Glu Tyr Asp Asn Gly Gly Glu Leu Val Ala Val
                85                  90                  95

Lys Ser Phe Lys Tyr His Glu Gly Tyr Asn Pro Glu Thr Met Val Asn
            100                 105                 110

Asp Val Ala Val Ile Lys Leu Ala Thr Pro Val Arg Glu Ser Ser Lys
        115                 120                 125

Val Arg Tyr Val Lys Leu Ala Glu Lys Thr Pro Ala Thr Gly Thr Pro
130                 135                 140

Ala Val Val Thr Gly Trp Gly Ser Lys Cys Phe Leu Phe Cys Gln Thr
145                 150                 155                 160

Ala Pro Lys Val Leu Gln Lys Val Glu Val Asp Ile Val Asp Glu Lys
                165                 170                 175

Thr Cys Ala Ser Ser Glu Tyr Lys Tyr Gly Asp Ile Lys Glu Thr
            180                 185                 190

Met Leu Cys Ala Tyr Ala Val Lys Lys Asp Ala Cys Gln Gly Asp Ser
        195                 200                 205

Gly Gly Pro Leu Val Ala Asn Asn Lys Leu Val Gly Val Val Ser Trp
210                 215                 220

Gly Lys Gly Cys Ala Leu Ala Gly Tyr Pro Gly Val Tyr Cys Asp Val
225                 230                 235                 240

Ala Thr Val Arg Ser Trp Ile Glu Lys Thr Ala Lys Ser Leu
                245                 250

<210> SEQ ID NO 3
<211> LENGTH: 687
<212> TYPE: DNA
<213> ORGANISM: Lucilia sericata

<400> SEQUENCE: 3
attgtcaatg gtgtggatac caccattcag gcccatccct atcaggtttc tttgcaaacc      60
aacaatggtt tccatttctg cggtggttcc atcatcagcg aagacattat tgtaactgct     120
gctcattgca tgcaatccta caaggcctac caattcaaag tacgtttggg ttccactgaa     180
tacgataatg gtggtgaatt ggttgccgtc aagtctttca ataccacga aggttacaat      240 cccgaaacca tggttaatga tgttgccgtt atcaaattag ccactccagt gcgtgaatct     300
tccaaggtac gttatgttaa attggctgag aagacacctg ctactggcac cccagctgtc     360
gttactggtt ggggttctaa gtgcttcttg ttctgccaaa ctgcccctaa agttttgcaa     420
aaggttgagg tcgatattgt tgatgagaag acctgcgctt ccagcgaata caaatatggt     480
gatgacatca aggaaactat tgttgtgtgct tatgctgtta agaaggatgc ttgccaaggt     540
gattctggtg gtccttttggt tgccaacaac aaattggtcg tgttgttttc tggggtaaa    600 ggttgtgccc ttgctggcta tcccggtgta tactgcgatg ttgctactgt ccgcagctgg    660
attgaaaaga ctgccaagag tttgtaa                                         687

<210> SEQ ID NO 4
<211> LENGTH: 228
<212> TYPE: PRT
<213> ORGANISM: Lucilia sericata
```

```
<400> SEQUENCE: 4

Ile Val Asn Gly Val Asp Thr Thr Ile Gln Ala His Pro Tyr Gln Val
1               5                   10                  15

Ser Leu Gln Thr Asn Asn Gly Phe His Phe Cys Gly Gly Ser Ile Ile
                20                  25                  30

Ser Glu Asp Ile Ile Val Thr Ala Ala His Cys Met Gln Ser Tyr Lys
            35                  40                  45

Ala Tyr Gln Phe Lys Val Arg Leu Gly Ser Thr Glu Tyr Asp Asn Gly
        50                  55                  60

Gly Glu Leu Val Ala Val Lys Ser Phe Lys Tyr His Glu Gly Tyr Asn
65                  70                  75                  80

Pro Glu Thr Met Val Asn Asp Val Ala Val Ile Lys Leu Ala Thr Pro
                85                  90                  95

Val Arg Glu Ser Ser Lys Val Arg Tyr Val Lys Leu Ala Glu Lys Thr
                100                 105                 110

Pro Ala Thr Gly Thr Pro Ala Val Val Thr Gly Trp Gly Ser Lys Cys
            115                 120                 125

Phe Leu Phe Cys Gln Thr Ala Pro Lys Val Leu Gln Lys Val Glu Val
130                 135                 140

Asp Ile Val Asp Glu Lys Thr Cys Ala Ser Ser Glu Tyr Lys Tyr Gly
145                 150                 155                 160

Asp Asp Ile Lys Glu Thr Met Leu Cys Ala Tyr Ala Val Lys Lys Asp
                165                 170                 175

Ala Cys Gln Gly Asp Ser Gly Gly Pro Leu Val Ala Asn Asn Lys Leu
            180                 185                 190

Val Gly Val Ser Trp Gly Lys Gly Cys Ala Leu Ala Gly Tyr Pro
                195                 200                 205

Gly Val Tyr Cys Asp Val Ala Thr Val Arg Ser Trp Ile Glu Lys Thr
210                 215                 220

Ala Lys Ser Leu
225

<210> SEQ ID NO 5
<211> LENGTH: 717
<212> TYPE: DNA
<213> ORGANISM: Lucilia sericata

<400> SEQUENCE: 5
ggcgctattc ccaatgattt ggatggccgc attgtcaatg gtgtggatac caccattcag     60
gcccatccct atcaggtttc tttgcaaacc aacaatggtt tccatttctg cggtggttcc    120
atcatcagcg aagacattat tgtaactgct gctcattgca tgcaatccta caaggcctac    180
caattcaaag tacgtttggg ttccactgaa tacgataatg gtggtgaatt ggttgccgtc    240
aagtctttca ataccacga aggttacaat cccgaaacca tggttaatga tgttgccgtt    300
atcaaattag ccactccagt gcgtgaatct tccaaggtac gttatgttaa attggctgag    360
aagacacctg ctactggcac cccagctgtc gttactggtt ggggttctaa gtgcttcttg    420
ttctgccaaa ctgcccctaa agttttgcaa aaggttgagg tcgatattgt tgatgagaag    480
acctgcgctt ccagcgaata caaatatggt gatgacatca aggaaactat gttgtgtgct    540
tatgctgtta gaaggatgc ttgccaaggt gattctggtg gtcctttggt tgccaacaac    600
aaattggtcg gtgttgtttc ctggggtaaa ggttgtgccc ttgctggcta tcccggtgta    660
tactgcgatg ttgctactgt ccgcagctgg attgaaaaga ctgccaagag tttgtaa      717
```

```
<210> SEQ ID NO 6
<211> LENGTH: 238
<212> TYPE: PRT
<213> ORGANISM: Lucilia sericata

<400> SEQUENCE: 6

Gly Ala Ile Pro Asn Asp Leu Asp Gly Arg Ile Val Asn Gly Val Asp
1               5                   10                  15

Thr Thr Ile Gln Ala His Pro Tyr Gln Val Ser Leu Gln Thr Asn Asn
            20                  25                  30

Gly Phe His Phe Cys Gly Gly Ser Ile Ile Ser Glu Asp Ile Ile Val
        35                  40                  45

Thr Ala Ala His Cys Met Gln Ser Tyr Lys Ala Tyr Gln Phe Lys Val
    50                  55                  60

Arg Leu Gly Ser Thr Glu Tyr Asp Asn Gly Glu Leu Val Ala Val
65                  70                  75                  80

Lys Ser Phe Lys Tyr His Glu Gly Tyr Asn Pro Glu Thr Met Val Asn
                85                  90                  95

Asp Val Ala Val Ile Lys Leu Ala Thr Pro Val Arg Glu Ser Ser Lys
            100                 105                 110

Val Arg Tyr Val Lys Leu Ala Glu Lys Thr Pro Ala Thr Gly Thr Pro
        115                 120                 125

Ala Val Val Thr Gly Trp Gly Ser Lys Cys Phe Leu Phe Cys Gln Thr
    130                 135                 140

Ala Pro Lys Val Leu Gln Lys Val Glu Val Asp Ile Val Asp Glu Lys
145                 150                 155                 160

Thr Cys Ala Ser Ser Glu Tyr Lys Tyr Gly Asp Asp Ile Lys Glu Thr
                165                 170                 175

Met Leu Cys Ala Tyr Ala Val Lys Lys Asp Ala Cys Gln Gly Asp Ser
            180                 185                 190

Gly Gly Pro Leu Val Ala Asn Asn Lys Leu Val Gly Val Ser Trp
        195                 200                 205

Gly Lys Gly Cys Ala Leu Ala Gly Tyr Pro Gly Val Tyr Cys Asp Val
    210                 215                 220

Ala Thr Val Arg Ser Trp Ile Glu Lys Thr Ala Lys Ser Leu
225                 230                 235

<210> SEQ ID NO 7
<211> LENGTH: 16
<212> TYPE: PRT
<213> ORGANISM: Lucilia sericata

<400> SEQUENCE: 7

Met Phe Arg Phe Val Ala Leu Phe Ala Phe Val Ser Cys Ala Leu Ala
1               5                   10                  15

<210> SEQ ID NO 8
<211> LENGTH: 10
<212> TYPE: PRT
<213> ORGANISM: Lucilia sericata

<400> SEQUENCE: 8

Ile Val Asn Gly Val Asp Thr Thr Ile Gln
1               5                   10

<210> SEQ ID NO 9
<211> LENGTH: 254
<212> TYPE: PRT
<213> ORGANISM: Lucilia sericata
```

-continued

<400> SEQUENCE: 9

```
Met Leu Arg Phe Ile Ala Val Phe Ala Leu Val Asn Cys Ala Leu Ala
1               5                   10                  15

Gly Thr Leu Pro Asn Asp Leu Asp Gly Arg Ile Val Asn Gly Val Asp
            20                  25                  30

Thr Thr Ile Glu Ala His Pro Tyr Gln Val Pro Leu Gln Asn Ala Ala
        35                  40                  45

Leu Ser His Phe Cys Gly Gly Ser Ile Ile Ser Glu Asp Leu Val Val
    50                  55                  60

Thr Ala Ala His Cys Met Gln Ser Tyr Thr Ala Ser Gln Ile Lys Val
65                  70                  75                  80

Arg Leu Gly Ser Thr Ile Tyr Asn Glu Gly Glu Leu Val Ser Val
                85                  90                  95

Lys Ala Phe Lys Phe His Glu Gly Tyr Asn Pro Lys Thr Met Val Asn
                100                 105                 110

Asp Val Ala Leu Ile Lys Leu Ala Thr Pro Val Arg Glu Ser Ser Lys
            115                 120                 125

Ile Arg Tyr Ile Arg Leu Ala Asp Arg Thr Pro Pro Thr Gly Thr Pro
130                 135                 140

Ala Val Val Thr Gly Trp Gly Thr Lys Cys Phe Leu Thr Cys Val Ser
145                 150                 155                 160

Leu Pro Lys Thr Leu Gln Glu Val Glu Val Asp Ile Val Asp Gln Lys
                165                 170                 175

Ala Cys Ala Ser Asn Glu Phe Lys Tyr Gly Ser Gln Ile Gln Asp Thr
            180                 185                 190

Met Val Cys Ala Tyr Ala Leu Lys Lys Asp Ala Cys Gln Gly Asp Ser
        195                 200                 205

Gly Gly Pro Leu Val Ala Asn Asn Gln Leu Val Gly Ile Val Ser Trp
    210                 215                 220

Gly Ser Gly Cys Ala Arg Val Gly Tyr Pro Gly Val Phe Cys Asp Val
225                 230                 235                 240

Pro Ser Val Arg Ser Trp Ile Glu Lys Thr Ala Lys Glu Leu
                245                 250
```

<210> SEQ ID NO 10
<211> LENGTH: 765
<212> TYPE: DNA
<213> ORGANISM: Lucilia sericata

<400> SEQUENCE: 10

```
atgttgcgtt tcatagctgt attcgcttta gttaactgtg ctttggccgg cactctgccc    60
aacgatttgg atggtcgtat tgttaacggt gttgatacta caattgaggc ccatccttat   120
caggttccat tgcaaaatgc tgctctcagt catttctgtg gtggatccat tatcagtgaa   180
gatctagttg ttactgctgc tcattgtatg caatcctata cggcttctca aattaaagtg   240
cgtttgggct ctactatata caatgaagga ggtgaattgg tatcagtaaa ggcttttaaa   300
ttccacgaag ttacaatcc taagacaatg gtgaatgacg ttgctcttat taaattggca   360
actccagtac gtgaatcgtc caaaatacgt tatattcgtt tggctgatcg tactccacct   420
actggtacgc cggctgtcgt tactggctgg ggtaccaagt gtttcttaac ctgtgttagt   480
ttgccaaaga ctttgcaaga agttgaagtt gatattgttg atcagaaagc ctgtgcttcc   540
aatgaattta atatggcag ccaaatacaa gacactatgg tatgtgctta cgcttttaaa   600
aaggatgctt gccaaggcga ctctggtggc ccattagtcg ctaataatca attggtcggt   660
```

-continued

```
attgtgtctt ggggtagtgg ttgcgctcgc gtcggctatc ctggtgtatt ctgtgatgtg      720
ccctctgtac gctcatggat cgaaaagact gccaaggaat tgtaa                      765
```